United States Patent [19]

Bredesen et al.

[11] Patent Number: 5,218,969
[45] Date of Patent: Jun. 15, 1993

[54] INTELLIGENT STETHOSCOPE

[75] Inventors: Mark S. Bredesen; Elliot D. Schmerler, both of Incline Village, Nev.

[73] Assignee: Blood Line Technology, Inc., Incline Village, Nev.

[21] Appl. No.: 628,482

[22] Filed: Dec. 17, 1990

Related U.S. Application Data

[63] Continuation of Ser. No. 153,719, Feb. 4, 1988, Pat. No. 5,010,889.

[51] Int. Cl.$^5$ .............................................. A61B 5/02
[52] U.S. Cl. .................................. 128/710; 128/715; 381/67
[58] Field of Search .............. 128/773, 695, 696, 700, 128/710, 715; 181/126, 130, 131; 381/67

[56] References Cited

U.S. PATENT DOCUMENTS

| | | |
|---|---|---|
| 3,830,228 | 8/1974 | Foner . |
| 3,858,005 | 12/1974 | Marshall et al. . |
| 3,985,121 | 10/1976 | Hellenbrand ........................ 128/715 |
| 4,170,717 | 10/1979 | Walshe . |
| 4,220,160 | 9/1980 | Kimball et al. . |
| 4,226,248 | 10/1980 | Manoli . |
| 4,246,784 | 1/1981 | Bowen . |
| 4,270,547 | 6/1981 | Steffen et al. . |
| 4,321,929 | 3/1982 | Lemelson et al. . |
| 4,362,164 | 12/1982 | Little et al. ........................ 128/715 |
| 4,396,018 | 8/1983 | Sibley . |
| 4,404,974 | 9/1983 | Titus . |
| 4,417,306 | 11/1983 | Citron et al. . |
| 4,422,458 | 12/1983 | Kravath . |
| 4,425,921 | 1/1984 | Fujisaki et al. . |
| 4,438,772 | 3/1984 | Slavin . |
| 4,459,993 | 7/1984 | Foreman . |
| 4,483,346 | 11/1984 | Slavin . |
| 4,494,551 | 1/1985 | Little, III et al. . |

(List continued on next page.)

OTHER PUBLICATIONS

"Algorithm for Detecting the First and Second Heart Sounds by Spectral Tracking," to Iwata et al., published in *Medical & Biological Engineering & Computing*, vol. 18, No. 1, Jan., 1980, describes a detection algorithm for locating the first and second heart sounds.

"Pattern Classification of the Phonocardiogram Using Linear Prediction Analysis," to Ewada et al., published in *Medical & Biological Engineering & Computing*, vol. 15, No. 4, Jul. 1977 describes the application of linear prediction analysis to extract the spectral pattern from phonocardiogram signals to assist an automatic diagnosis system. The diagnostic system or its construction is not described but merely suggested as an application for this technology.

*Primary Examiner*—William E. Kamm
*Assistant Examiner*—J. P. Lacyk
*Attorney, Agent, or Firm*—Merchant, Gould, Smith, Edell, Welter & Schmidt

[57] ABSTRACT

An intelligenet stethoscope for performing auscultation and for automatically diagnosing abnormalities based on body sounds is described in which the body sounds are received, digitized and stored in memory. The body sounds are recorded from a plurality of locations on the body, and all of the sounds are categorized according to specific characteristics to form a matrix of information. The generated matrix is then compared against a plurality of stored matrices using a technique similar to signature analysis. Each of the stored matrices contain information indicative of known abnormalities such as specific heart murmurs, lung abnormalities, etc. When a matrix match is found, the diagnosis is displayed on an LCD display formed in the body of the stethoscope. The LCD display is also capable of displaying a visual representation of the recorded body sounds. The resent invention is applicable to heart sounds, lung sounds, and bruits. A wide variety of heart and lung abnormalities along with their signatures are described and the specific steps required for the signature analysis is described.

14 Claims, 27 Drawing Sheets

U.S. PATENT DOCUMENTS

| | | |
|---|---|---|
| 4,506,678 | 3/1985 | Russell et al. . |
| 4,528,689 | 7/1985 | Katz . |
| 4,531,523 | 7/1985 | Anderson . |
| 4,537,202 | 8/1985 | Mancini et al. . |
| 4,549,551 | 10/1985 | Dyck et al. . |
| 4,565,201 | 1/1986 | Lass . |
| 4,566,461 | 1/1986 | Lubell et al. . |
| 4,569,356 | 2/1986 | Kyozuka . |
| 4,569,357 | 2/1986 | Sanz et al. . |
| 4,586,514 | 5/1986 | Schlager et al. . |
| 4,598,417 | 7/1986 | Deno . |
| 4,619,268 | 10/1986 | Uphold et al. . |
| 4,624,263 | 11/1986 | Slavin . |
| 4,635,645 | 1/1987 | Fukushima . |
| 4,649,930 | 3/1987 | Groch et al. . |
| 4,671,295 | 6/1987 | Abrams et al. . |
| 4,672,975 | 6/1987 | Sirota . |
| 4,672,976 | 6/1987 | Kroll . |
| 4,672,977 | 6/1987 | Kroll . |
| 4,679,570 | 7/1987 | Lund et al. . |
| 4,686,999 | 8/1987 | Snyder et al. . |
| 4,705,048 | 11/1987 | Pfohl . |
| 4,712,565 | 12/1987 | Katz et al. . |
| 4,719,923 | 1/1988 | Hartwell et al. . |
| 4,720,866 | 1/1988 | Elias et al. . |
| 4,759,374 | 7/1988 | Kierney et al. . |
| 4,763,663 | 8/1988 | Uphold et al. . |
| 4,770,189 | 9/1988 | Shyu . |
| 4,777,961 | 10/1988 | Saltzman . |
| 4,781,200 | 11/1988 | Baker . |
| 4,784,153 | 11/1988 | Marks . |
| 4,784,154 | 11/1988 | Shirley et al. . |
| 4,792,145 | 12/1988 | Eisenberg et al. . |
| 4,803,996 | 2/1989 | Peel et al. . |

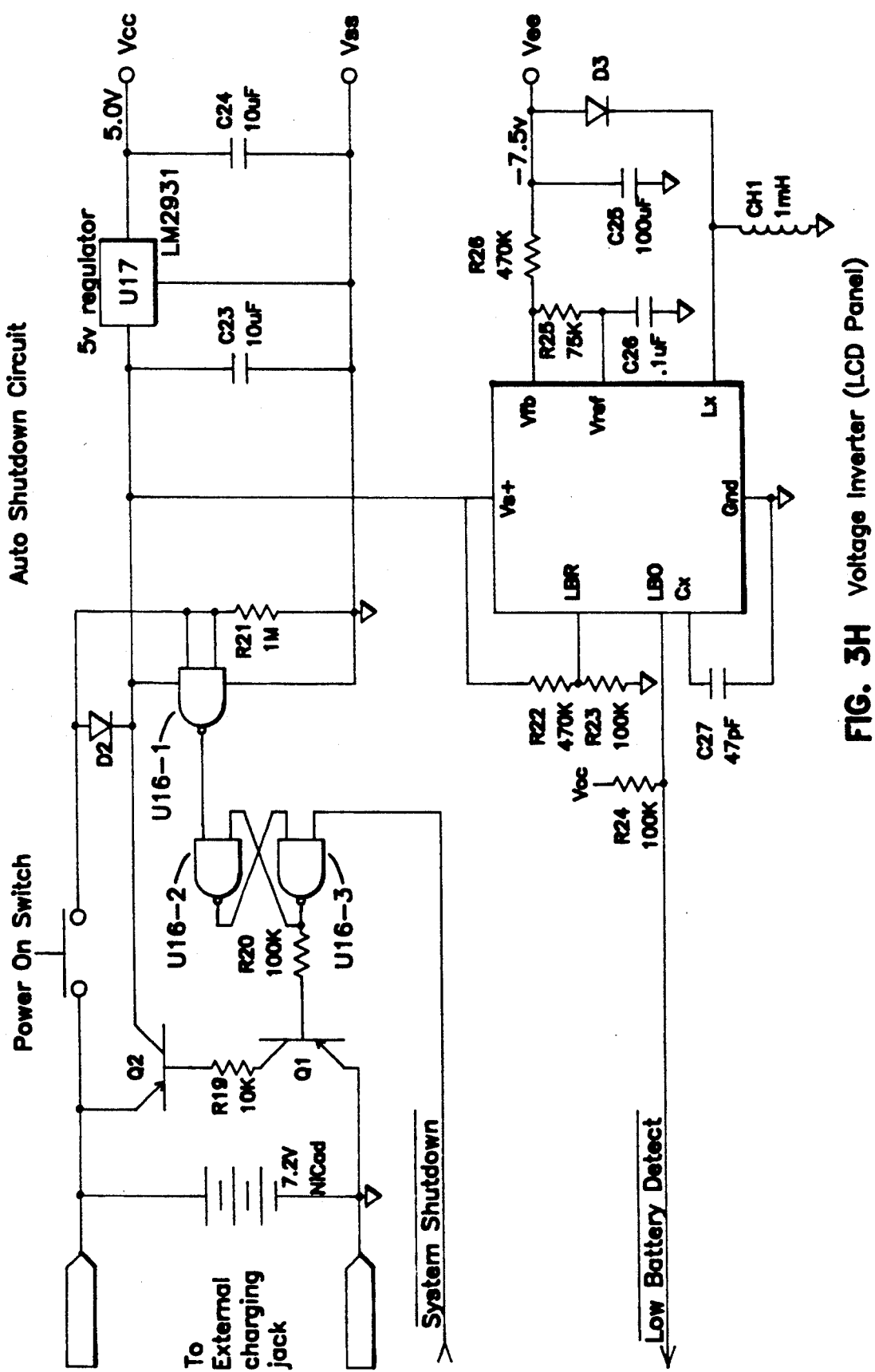
FIG. 3H Voltage Inverter (LCD Panel)

701

|     | A   | B   | C   | D   | E   | F   |
| --- | --- | --- | --- | --- | --- | --- |
| PMI |     |     |     |     |     | X   |
| 1   | Y   | Y   | Y   | Y   | Y   | Y   |
| 2   | Y   | Y   | Y   | Y   | Y   | Y   |
| 3   | Y   | Y   | Y   | Y   | Y   | Y   |
| 4   | Y   | Y   | Y   | Y   | Y   | Y   |
| 5   | N   | N   | N   | N   | N   | N   |
| 6   | N   | N   | N   | N   | N   | N   |
| 7   | Y   | Y   | N/Y | N/Y | N   | N   |
| 8   | N/Y | N/Y | N/Y | N/Y | N/Y | N/Y |

|     | A   | B   | C   | D   | E   | F   |
| --- | --- | --- | --- | --- | --- | --- |
| PMI |     |     |     |     |     | X   |
| 1   | Y   | Y   | Y   | Y   | Y   | Y   |
| 2   | Y   | Y   | Y   | Y   | Y   | Y   |
| 3   | Y   | Y   | Y   | Y   | Y   | Y   |
| 4   | Y   | Y   | Y   | Y   | Y   | Y   |
| 5   | N   | N   | N   | N   | N   | N   |
| 6   | N/Y | N/Y | N/Y | N/Y | N/Y | Y   |
| 7   | N/Y | N/Y | N/Y | N/Y | N/Y | Y   |
| 8   | N/Y | N/Y | N/Y | N/Y | N/Y | N   |

FIG. 7B

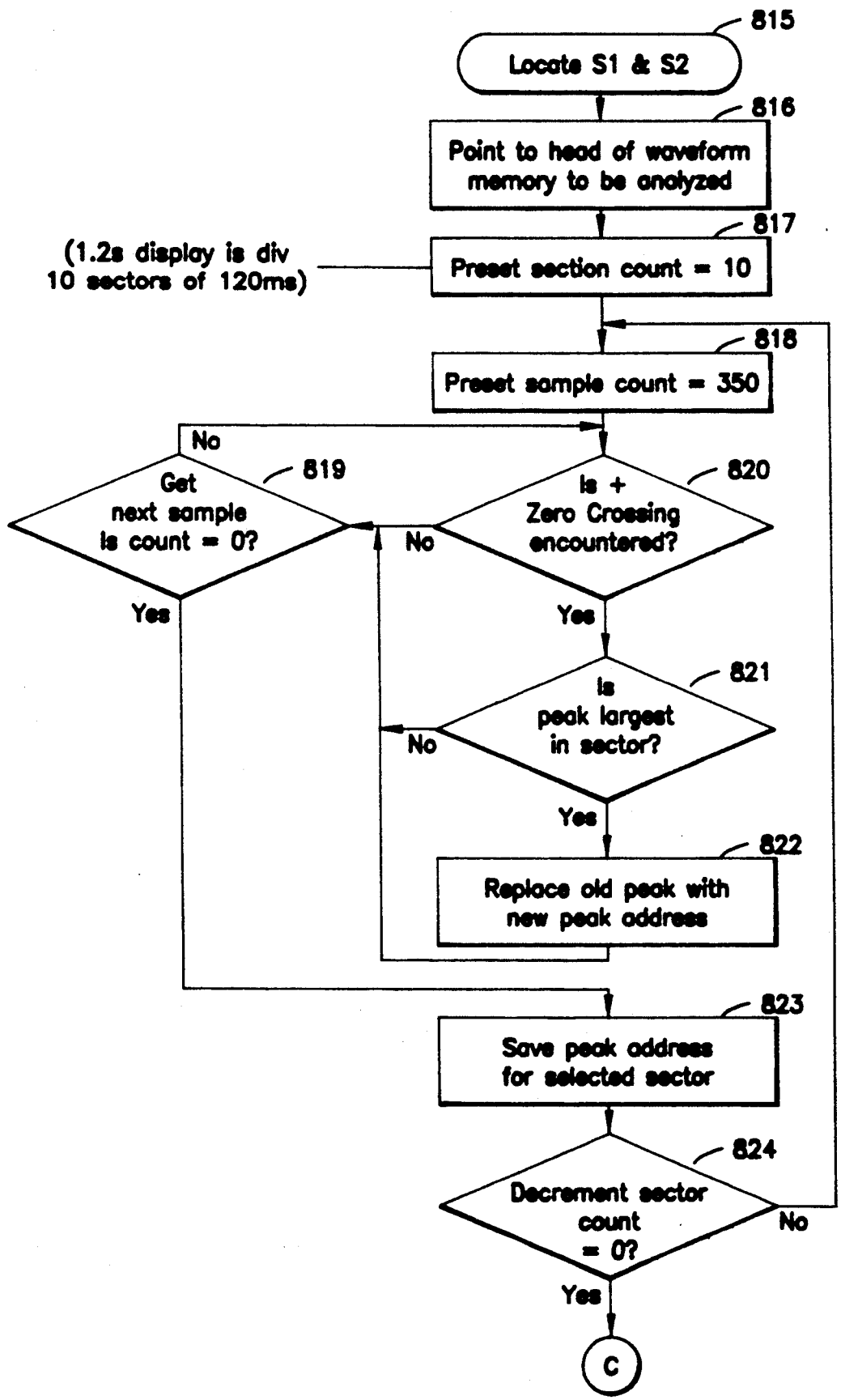
FIG. 8B (To FIG. 8C)

|     | A   | B   | C   | D   | E   | F   |
| --- | --- | --- | --- | --- | --- | --- |
| PMI | X   |     |     |     |     |     |
| 1   | Y   | Y   | Y   | Y   | Y   | Y   |
| 2   | Y   | Y   | Y   | Y   | Y   | Y   |
| 3   | Y   | Y   | Y   | Y   | Y   | Y   |
| 4   | Y   | Y   | Y   | Y   | Y   | Y   |
| 5   | Y   | N/Y | N/Y | N/Y | N/Y | N/Y |
| 6   | N   | N   | N   | N   | N   | N   |
| 7   | N/Y | N/Y | N/Y | N/Y | N   | N   |
| 8   | N/Y | N/Y | N/Y | N/Y | N/Y | N/Y |

FIG. 9A

|     | A   | B   | C   | D   | E   | F   |
| --- | --- | --- | --- | --- | --- | --- |
| PMI |     |     | X   |     |     |     |
| 1   | Y   | Y   | Y   | Y   | Y   | Y   |
| 2   | Y   | Y   | Y   | Y   | Y   | Y   |
| 3   | Y   | Y   | Y   | Y   | Y   | Y   |
| 4   | Y   | Y   | Y   | Y   | Y   | Y   |
| 5   | N   | N   | N   | N   | N   | N   |
| 6   | N/Y | N/Y | Y   | N/Y | N/Y | N/Y |
| 7   | N/Y | N/Y | N/Y | N/Y | N   | N   |
| 8   | N/Y | N/Y | N/Y | N/Y | N/Y | N/Y |

FIG. 9B

|     | A   | B   | C   | D   | E   | F   |
| --- | --- | --- | --- | --- | --- | --- |
| PMI |     |     |     |     |     | X   |
| 1   | Y   | Y   | Y   | Y   | Y   | Y   |
| 2   | Y   | Y   | Y   | Y   | Y   | Y   |
| 3   | Y   | Y   | Y   | Y   | Y   | Y   |
| 4   | N/Y | N/Y | N/Y | N/Y | N/Y | N/Y |
| 5   | N/Y | N/Y | N/Y | N/Y | N/Y | Y   |
| 6   | N   | N   | N   | N   | N   | N   |
| 7   | N/Y | N/Y | N/Y | N/Y | N/Y | N/Y |
| 8   | N/Y | N/Y | N/Y | N/Y | N/Y | N/Y |

FIG. 9C

|     | A   | B   | C   | D   | E   | F   |
| --- | --- | --- | --- | --- | --- | --- |
| PMI |     |     |     |     | X   |     |
| 1   | Y   | Y   | Y   | Y   | Y   | Y   |
| 2   | Y   | Y   | Y   | Y   | Y   | Y   |
| 3   | Y   | Y   | Y   | Y   | Y   | Y   |
| 4   | Y   | Y   | Y   | Y   | Y   | Y   |
| 5   | N   | N   | N   | N   | N   | N   |
| 6   | N/Y | N/Y | N/Y | N/Y | Y   | N/Y |
| 7   | N/Y | N/Y | N/Y | N/Y | N/Y | N/Y |
| 8   | N/Y | N/Y | N/Y | N/Y | N/Y | N/Y |

FIG. 9D

|   | A | B | C | D | E | F |
|---|---|---|---|---|---|---|
| 1 | Y | Y | Y | Y | Y | Y |
| 2 | N | N | N | N | N | N |
| 3 | N | N | N | N | N | N |
| 4 | N | N | N | N | N | N |
| 5 | N | N | N | N | N | N |
| 6 | 50 | 50 | 50 | 50 | 50 | 50 |

|   | A | B | C | D | E | F |
|---|---|---|---|---|---|---|
| 1 | Y | Y | Y | Y | Y | N |
| 2 | N | N | N | N | N | Y |
| 3 | N | N | N | N | N | N |
| 4 | N | N | N | N | N | N |
| 5 | N | N | N | N | N | N |
| 6 | 50 | 50 | 50 | 50 | 50 | 50 |

INTELLIGENT STETHOSCOPE

This is a continuation of application Ser. No. 07/153,719, filed on Feb. 4, 1988, now U.S Pat, No. 5,010,889.

FIELD OF INVENTION

The present invention relates to diagnostic auscultation and in particular to automatic diagnosis and analysis of sounds made by the various body structures through the use of signature analysis.

BACKGROUND OF THE INVENTION

Analysis of heart, lung and vascular disorders by means of noninvasive auscultation has long been a very useful tool for medical diagnosis of ailments. By using a stethoscope, a physician would listen to the heart sounds, chest sounds or other body sounds to identify sounds associated with abnormalities. The most common of these are heart murmurs which when identified indicate specific abnormalities in the functioning of the heart. However, identifying specific murmurs, like identifying heart sounds, is difficult. Developing the skill to make a proper analysis takes years of study and practice. Acquiring expertise in identifying heart sounds and murmurs takes experience that many physicians do not have the opportunity to acquire, since many heart murmurs are very rare and are seldom encountered by general practitioners.

With the advent of the modern electronic stethoscope, a visual indication of heart sounds or chest sounds can be made-which aids in diagnosis. Electronic stethoscopes allow the physician to discern subtle differences in the frequency, intensity and duration of many sounds. However, it is still incumbent on the physician to correctly analyze the recorded and displayed sounds and diagnose the underlying abnormalities therefrom.

Due to the rarity of many heart murmurs and other body sounds, recognition and correct diagnosis of such sounds from displays or from listening directly to the body sounds is difficult or impossible for the inexperienced physician. Hence, there is a need in the medical arts for automatic recognition and diagnosis of abnormalities detected from body sounds. In particular, cardiovascular abnormalities need to be detected through auscultation methods and diagnosed automatically.

SUMMARY OF THE INVENTION

An intelligent stethoscope method and apparatus for performing auscultation and for automatically diagnosing abnormalities based on the body sounds is described in which the body sounds are received, digitized and stored in a memory. The body sounds are recorded from a plurality of locations on the body and all of the sounds are categorized according to specific characteristics to form an array of information. This array of information is compared against stored arrays of information using a technique similar to signature analysis. The stored arrays of information are indicative of known abnormalities such as specific heart murmurs, lung abnormalities, etc. When an array match is determined, the operator is informed and the diagnosis is displayed.

The apparatus and method for performing automatic diagnosis through auscultation is described as applicable to heart sounds, lung sounds, bruits, and other body sounds. The technique for forming and storing the arrays indicative of a large number of abnormalities in the heart and lungs can be stored within this apparatus to allow a wide variety of modes of operation and diagnostic abilities. The apparatus includes an LCD display which is capable of displaying along a linear time axis the analog view of the recorded body sound. The display also prompts the user as to the use of the device. The apparatus includes a keypad by which the operator controls the functions of the device.

BRIEF DESCRIPTION OF THE DRAWINGS

In the drawings, where like numerals refer to like components throughout the several views.

FIGS. 3a, 3b, 3c, 3d, 3e, 3f, 3g and 3h comprise the detailed electrical schematic diagrams of the microprocessor-based intelligent stethoscope, and are to be viewed together;

FIGS. 7a and 7b shows the construction of specific matrices from waveform data and includes a normal heart sounds matrix and a mitral stenosis matrix., FIGS. 8a, 8b, 8c, 8d, 8e, 8f, 8g and 8h are detailed flow charts of the diagnostic software used by the intelligent stethoscope to diagnose heart murmurs;

FIGS. 9a, 9b, 9c and 9d show the matrices used for diagnosing Valvular Aortic Stenosis, Aortic Regurgitation, Mitral Regurgitation and Tricuspid Stenoses, respectively;

DETAILED DESCRIPTION OF THE PREFERRED EMBODIMENT

In the following detailed description of the preferred embodiment, reference is made to the accompanying drawings which form a part hereof, and in which is shown by way of illustration a specific embodiment in which the invention may be practiced. This embodiment is described in sufficient detail to enable those skilled in the art to practice the invention, and it is to be understood that other embodiments may be utilized and that structural changes may be made without departing from the scope of the present invention. The following detailed description is, therefore, not to be taken in a limiting sense, and the scope of the present invention is defined by the appended claims.

Figure 1:
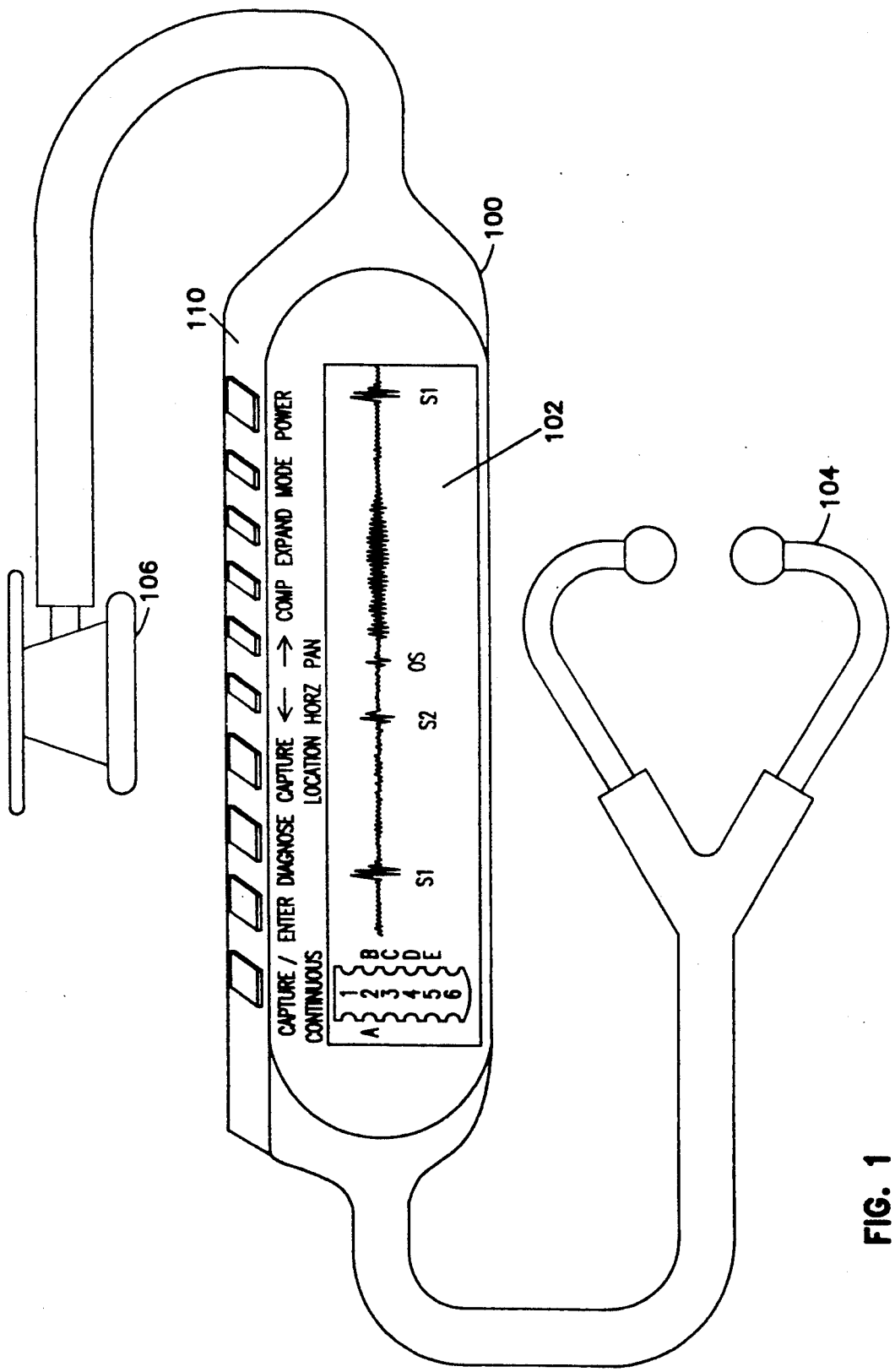
FIG. 1 is a pictorial view of the apparatus implementing the preferred embodiment of the present invention.

Referring to FIG. 1, the preferred embodiment of the present invention looks like other conventional stethoscopes with the addition of a center piece 100 which will house the electronics and display. The instrument uses an electronic interface coupled to the acoustic stethoscope to create an intelligent stethoscope, capable of processing cardiac sounds detected from the chest wall. The instrument digitizes the heart sounds and displays them on an LCD graphics panel 102 for the user to immediately review what he has heard simultaneously with the earpieces 104. All heart sounds are displayed in detail for easy review and diagnosis.

The instrument is capable of recognizing unique waveform patterns through a waveform signature analysis procedure in conjunction with a unique medical algorithm for the diagnosis of cardiac murmurs as well as detecting normal cardiac tones. The diagnosis is displayed upon command next to the waveform pattern. The instrument consists of a conventional stethoscope bell 106, acoustically coupled to an electronic interface. The audio signals are processed and digitized via a sampled analog to digital waveform acquisition procedure. The digitized audio is stored in data base memory for further analysis, while simultaneously being displayed on the LCD graphics panel display 102.

Also included as part of the instrument, is a keypad 110 which allows visual magnification of the display, along with controlling the operation of the microprocessor based stethoscope. There is also a peripheral data port (not shown) which is used for the transfer of data base memory to a digital plotter, and/or storage in a larger memory media. The system is powered from rechargeable batteries, and controlled by an intelligent power control system. If left unattended, the system will shut itself off while still retaining data base memory. There also exists a low battery detection circuit which will alert the user of that condition.

Hardware Description

Figure 2:
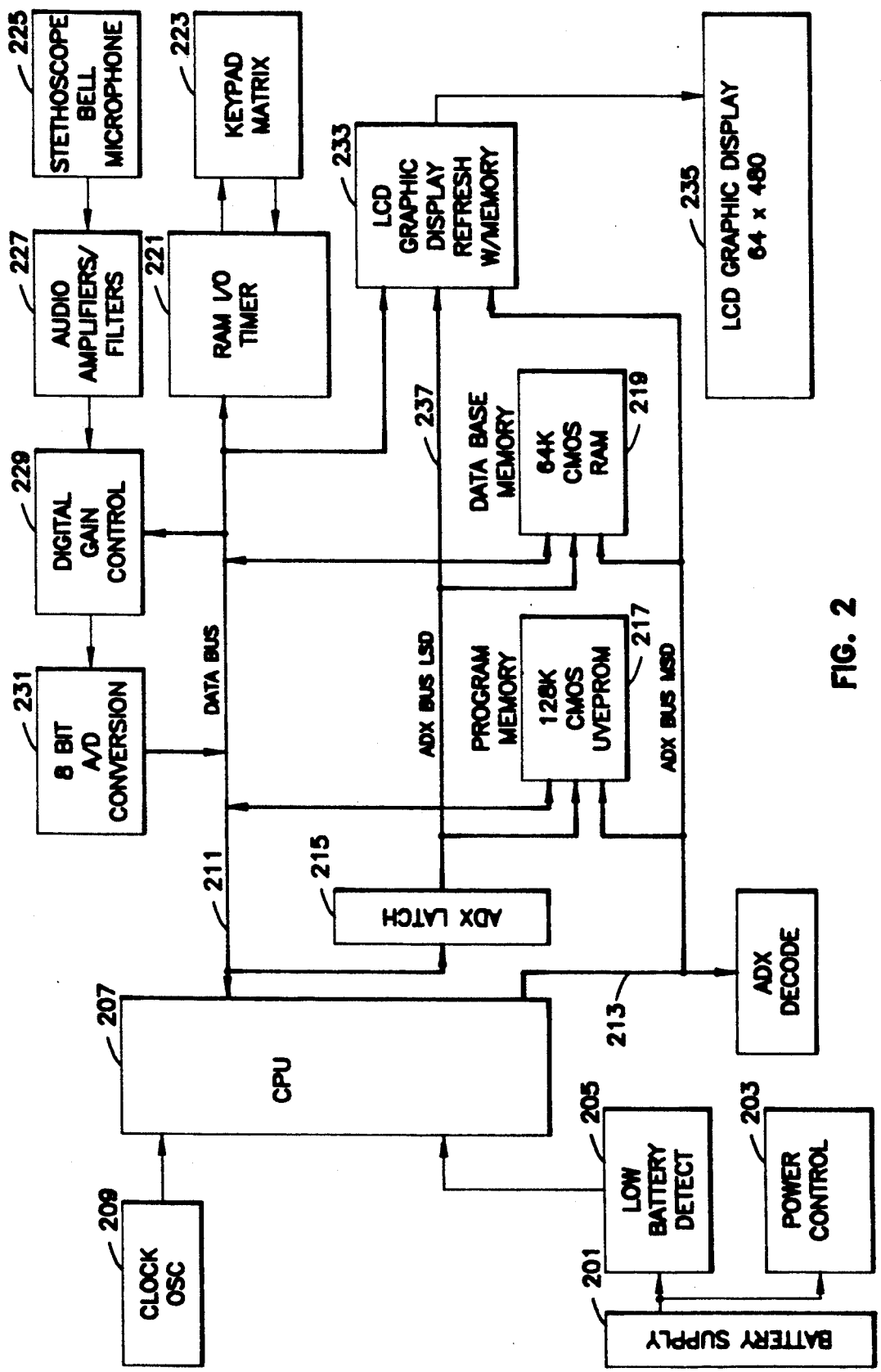
FIG. 2 is a block diagram of the microprocessor-based intelligent stethoscope.

Referring to FIG. 2, a block diagram of the microprocessor-based architecture of the intelligent stethoscope is shown. The battery supply 201 is used to power the electrical circuits of the intelligent stethoscope, the power connections being omitted for clarity in the block diagram. The power control circuit 203 contains an auto shutdown circuit, a voltage regulator, and a voltage inverter section to generate a plurality of voltages from the single voltage derived from the battery supply 201. A low battery detect circuit 205 monitors the voltage level in the batteries and reports this condition to CPU 207.

An NSC800 microprocessor available from National Semiconductor forms the CPU 207 in the microprocessor-based architecture of the intelligent stethoscope. Those skilled in the art will readily recognize that a wide variety of microprocessor types and microcontrollers can be used to implement the functions of the present invention. The preferred implementation uses an NSC800 microprocessor due to its availability and convenience in programming.

Clock oscillator 209 is used to generate the timing signals required by CPU 207 and to synchronize the functioning of the intelligent stethoscope. Those skilled in the art will readily recognize the variety of implementations of oscillator circuit 209 and the need for such a circuit.

The architecture of the present design shown in FIG. 2 is bus-oriented with a multiplexed address-data bus 211 for the low-ordered 8 bits and a dedicated address bus 213 for the high-ordered 8 bits of the address. The address latch 215 is needed for proper decoding of the low-ordered address bits for addressing the memories 217 and 219.

The RAM and I/O timer circuit 221 is in the preferred embodiment a multi-function chip part number NSC810 also available from National Semiconductor and designed specifically to interface with the NSC800 microprocessor. This circuit 221 contains its own data and address decoding logic to effectively interface with data bus 211. The RAM and I/O timer circuit 221 monitors selected functions within the intelligent stethoscope and interfaces to a keypad matrix 223 corresponding to the keypad 110 found on the intelligent stethoscope body 100. Keypad matrix 223 is used to enter command functions by the operator and to control the display.

Across the top of FIG. 2 is the input path for receiving the body sounds through the stethoscope bell microphone 225 found in the stethoscope bell 106. This microphone is attached to a high-gain audio amplifier and filter circuit 227 which in turn drives the digital gain control circuit 229. The gain of circuit 229 is digitally controlled off data bus 211 from CPU 207. The appropriate gain being programmed into gain control circuit 229 allows the correct amplification of the audio signals for appropriate analog to digital conversion by A/D converter 231. The results of the digitized audio signals is placed on data bus 211 for processing by CPU 207.

The program memory for operating the intelligent stethoscope is contained in memory circuit 217. This software, described in detail below, performs the appropriate signature analysis on the body sounds received from the stethoscope bell 106 and displayed by the LCD graphic display 235. The display and analysis requires working memory located in database memory 219. This read/write type of memory is used for, among other things, analysis of the body sounds received.

The LCD graphic display 235 is in the preferred embodiment a 64×480 pixel display capable of displaying analog representations of the body sounds, commands as to where to listen for the next body sound, and the results of the signature analysis and diagnosis of the body sounds. The LCD graphic display 235 is microprocessor-driven through controller 233. The details of the hardware design are described below.

Referring now to FIGS. 3a–3e, the detailed electrical design of the intelligent stethoscope will be described. The main power for the system is derived from a nominal 7.2 v NiCad rechargeable battery 302. The power control consists of three sections: an auto shutdown circuit, a 5 v Vcc regulator, and a voltage inverter section to generate a −7.5 v Vee.

Figure 3A:
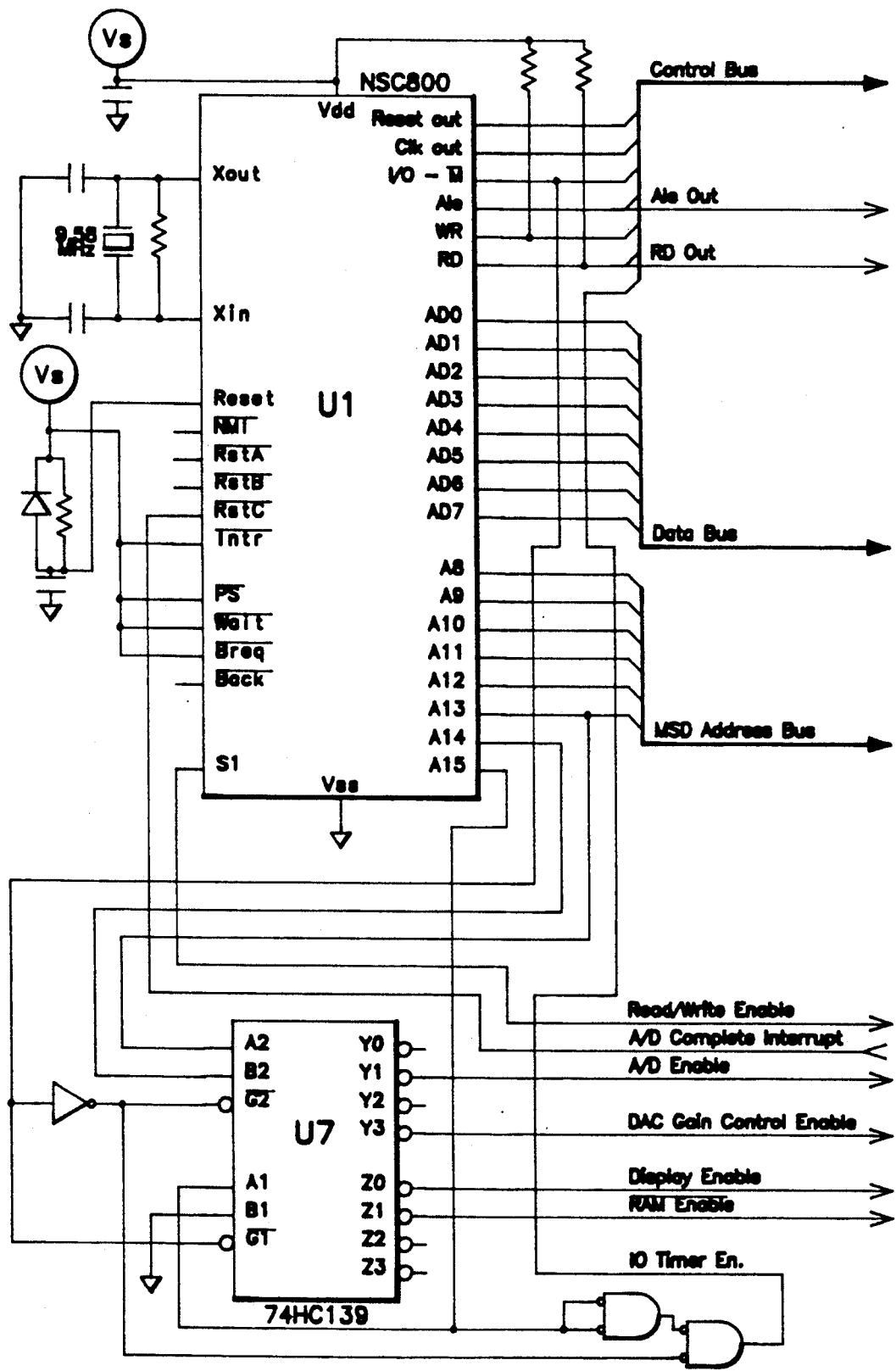
Figure 3B:
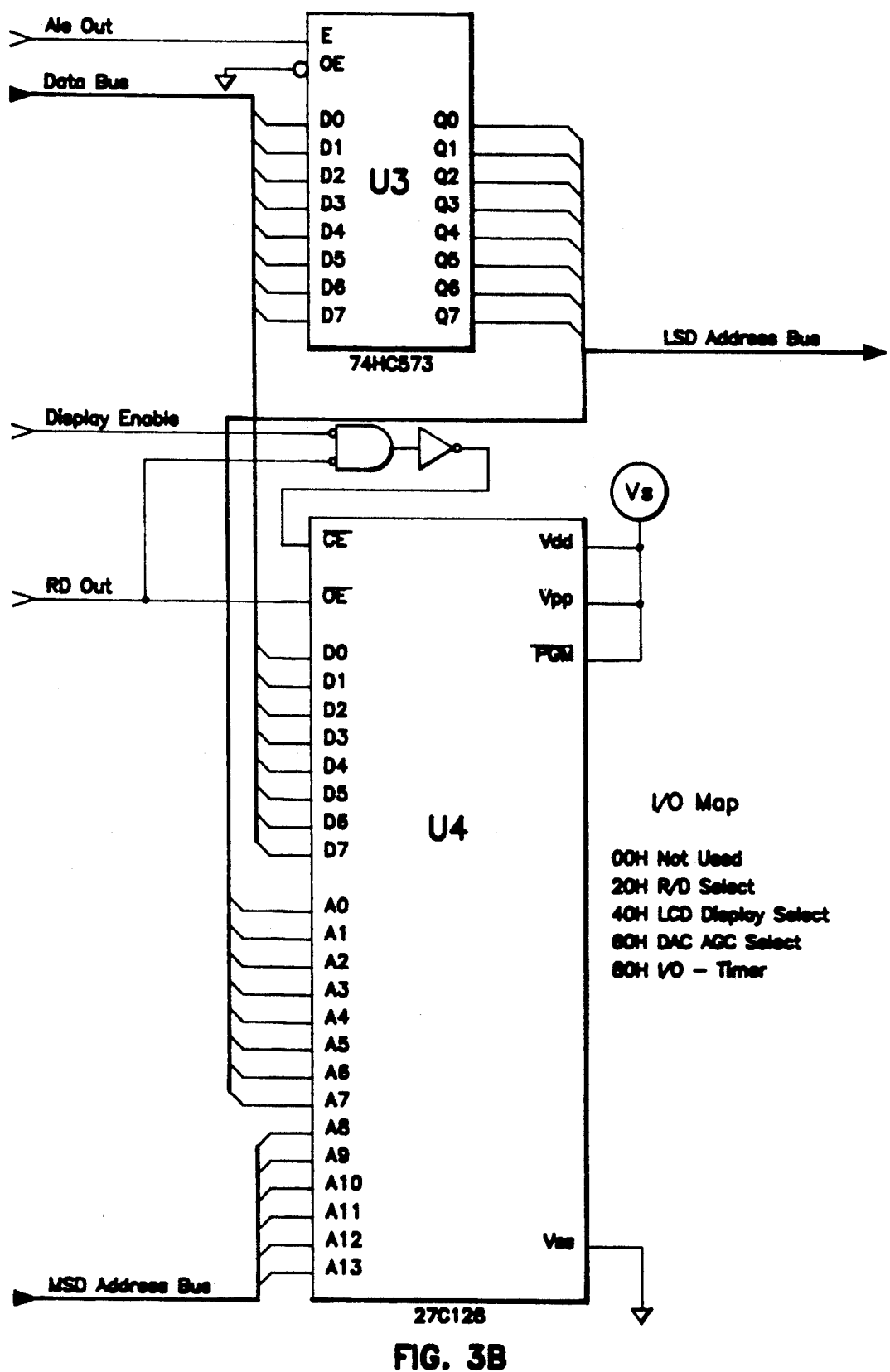
Figure 3C:
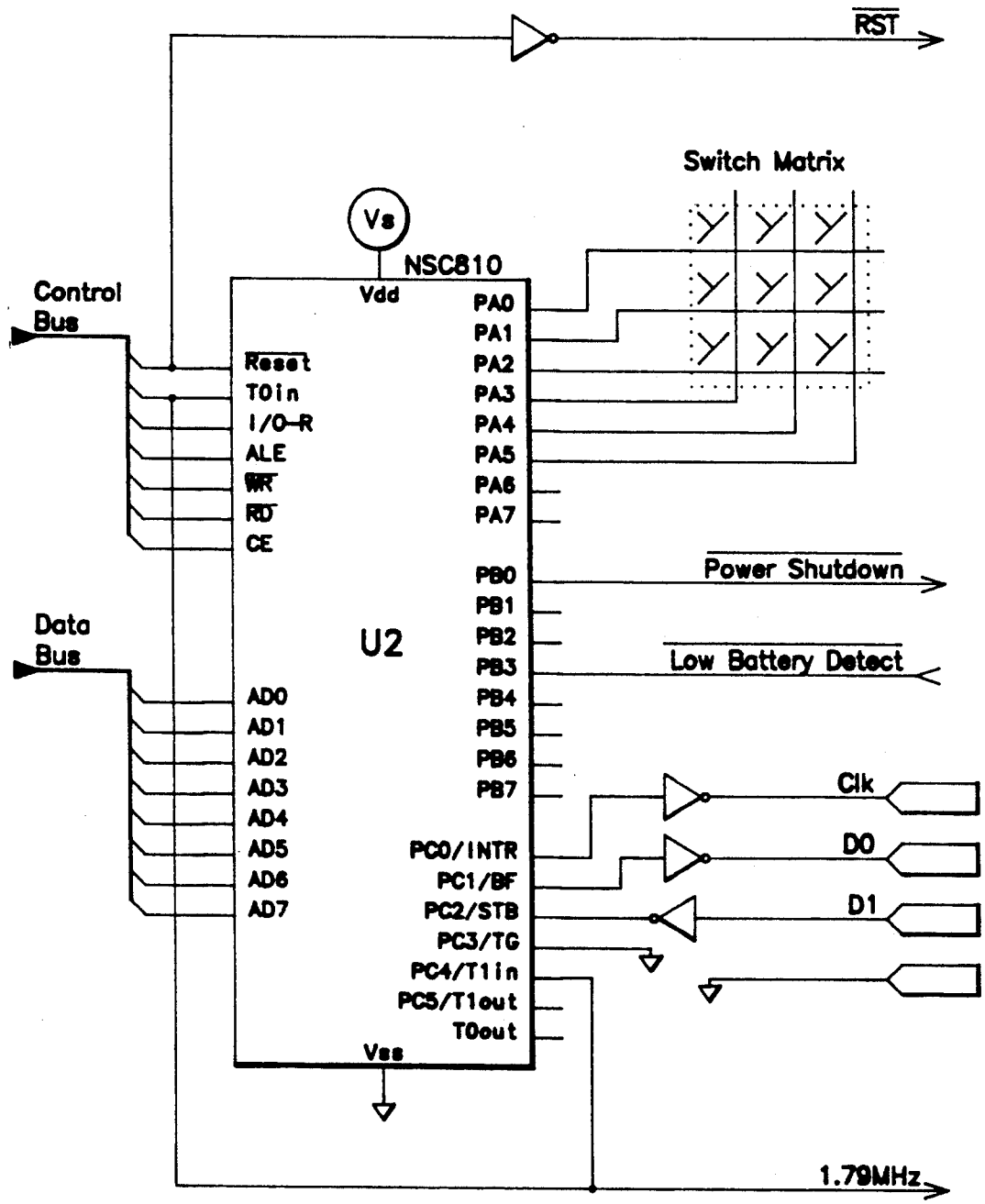
Figure 3D:
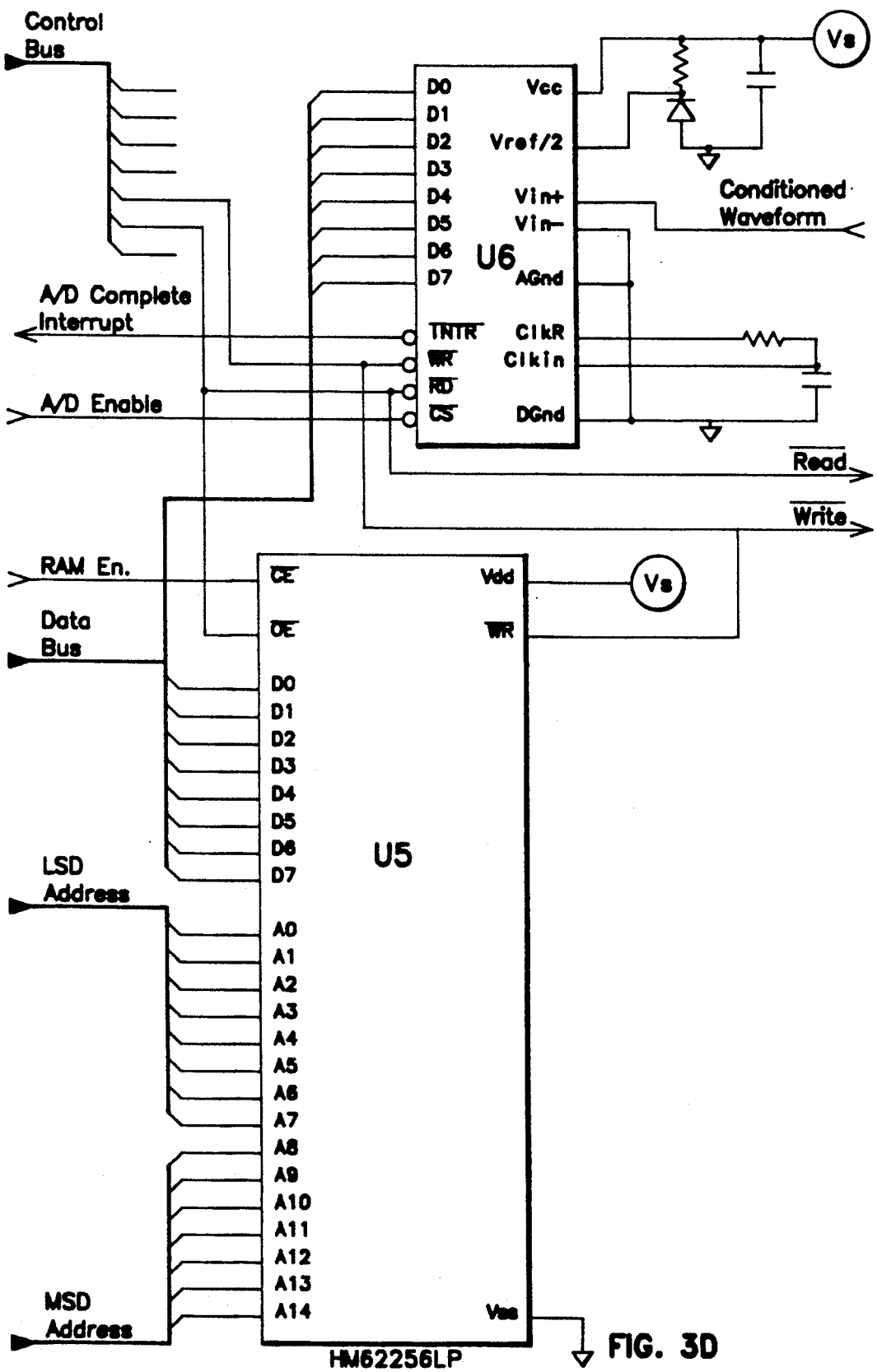
Figure 3E:
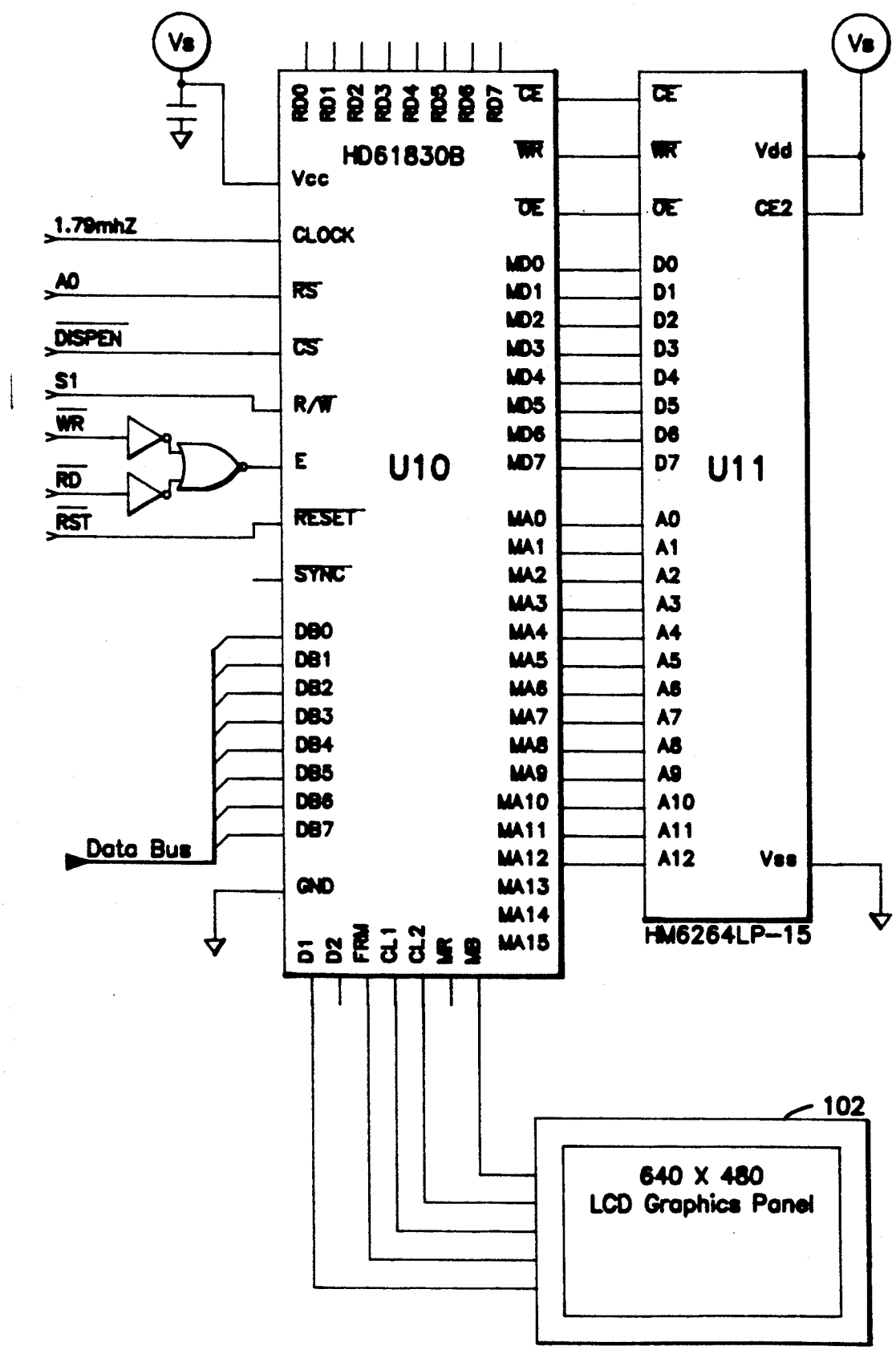
Figure 3F:
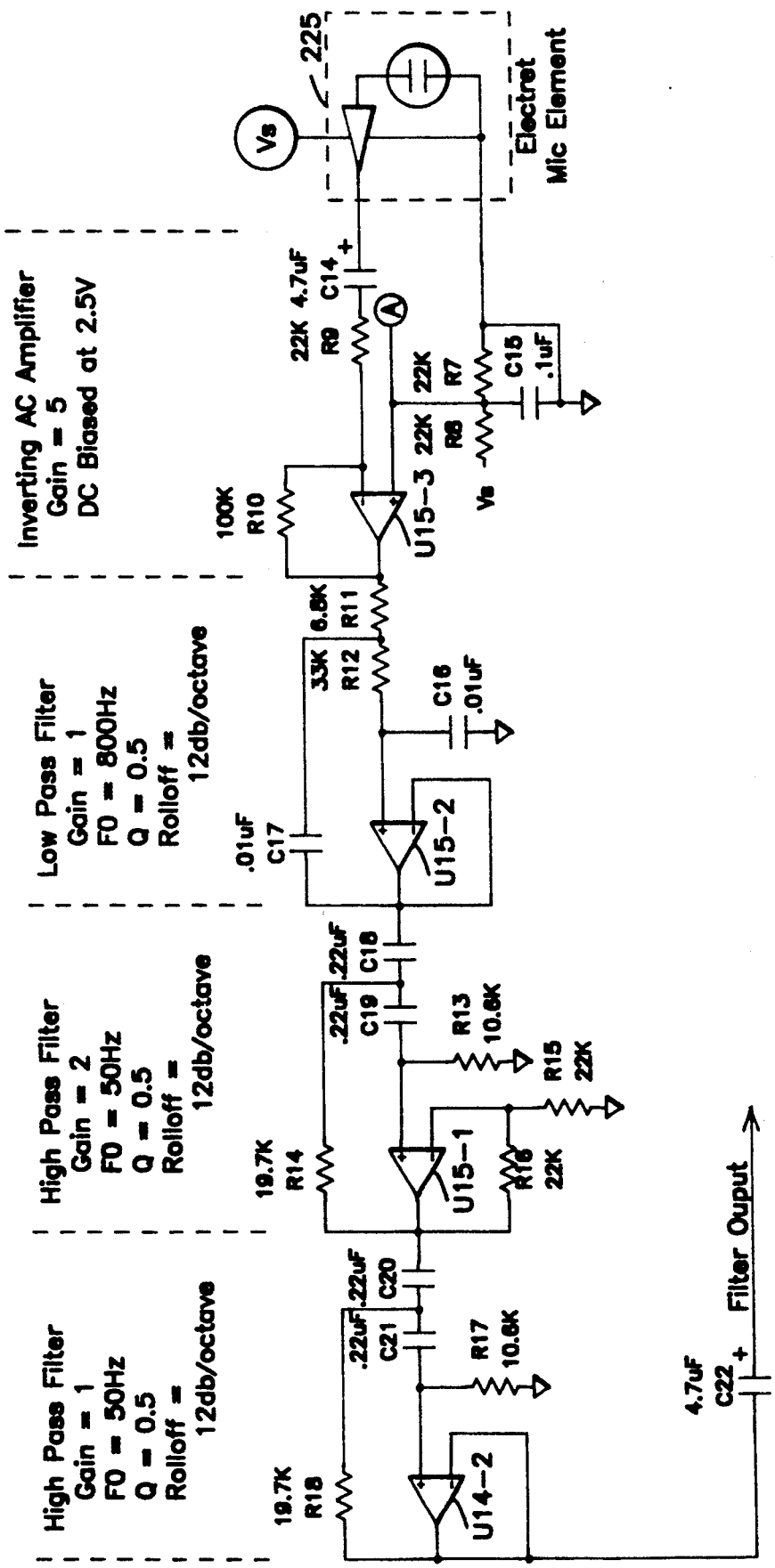
Figure 3G:
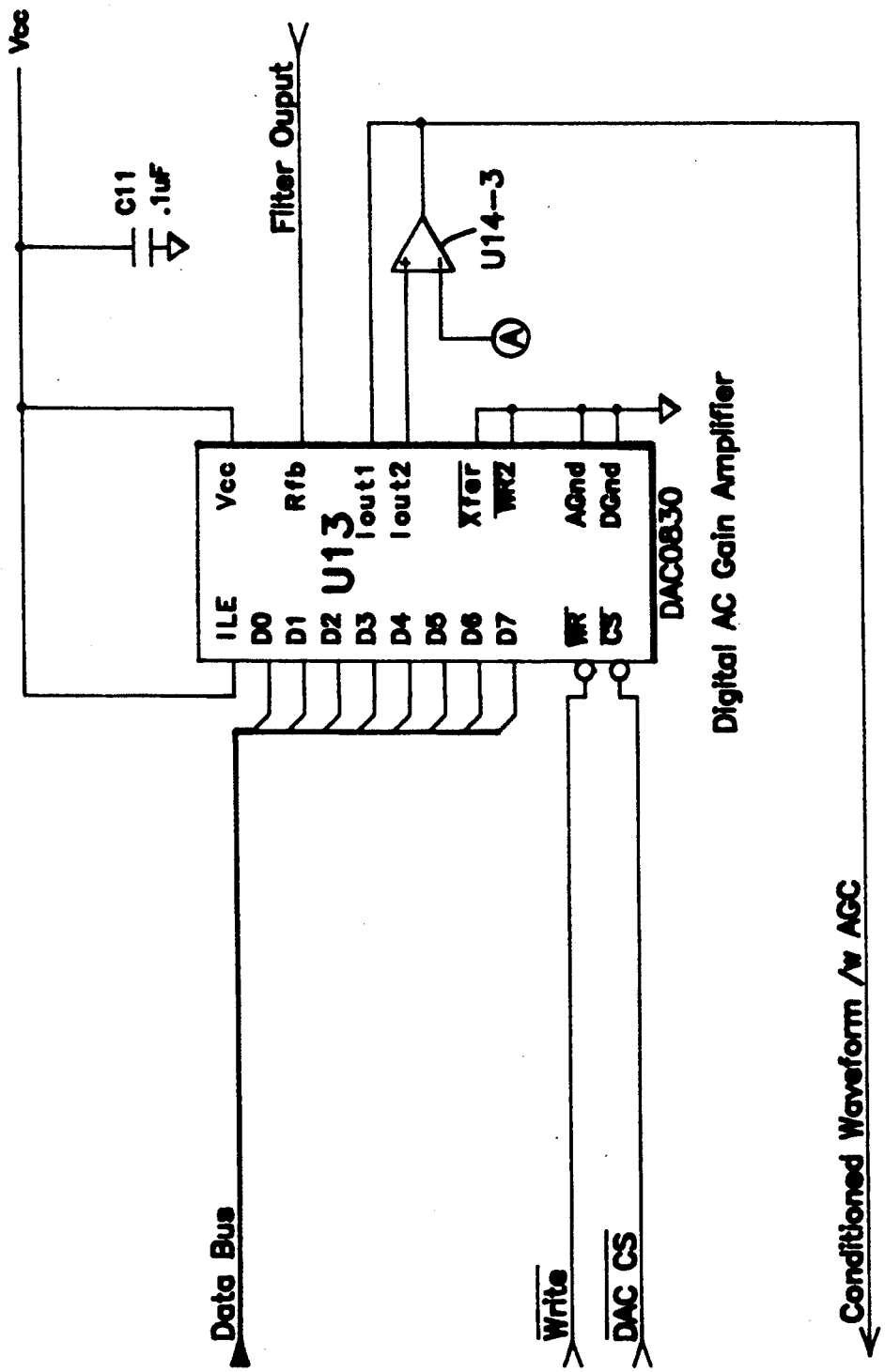

The auto shutdown circuit of FIG. 3e is activated by closing the momentary "Power On" switch found on the body 100 of the intelligent stethoscope. Battery voltage Vbb is switched to U16 and also the logic 1 voltage level at U16-1 sets the RS flip flop built from U16-2 and U16-3. The output of the RS flip-flop turns on NPN transistor Q1, the collector of which sinks current to the base of PNP transistor Q2. Q2 switches the battery voltage Vbb to the flip flop and also the input of the monolithic voltage regulator U17 which, in the preferred embodiment is part number LM2931 available from National Semiconductor and other vendors. The output of regulator U17 supplies a current limited and thermal protected 5 v dc labeled Vcc. System common is labeled Vss.

Upon Q2 switching on, the Vbb (battery voltage) is also input to the voltage inverter circuit comprised primarily of integrated circuit U18. This circuit (part number MAX634 available from Maxim Semiconductor) creates a −7.5 VDC from the positive battery voltage. The circuit also performs low battery detection from an internal voltage comparator and reference. The power to the system remains on until directed by the CPU to reset the RS flip flop and shut off Q2 which shuts off system power via the SYSTEM SHUTDOWN signal line.

The intelligence of the stethoscope system is implemented by its Central Processing Unit (CPU) and memory shown in FIGS. 3a and 3b. The central processor U1 is an NSC800 which is an 8-bit CMOS bus-oriented processor. It implements a multiplexed address and data bus by which its peripherals exchange data. The memory is made up of 32 K×8 of CMOS PROM and 32 K×8 of CMOS RAM. The program memory U4 held in UV erasable PROM contains the system software implementing the system hardware drivers, and intelligent diagnostic algorithms. The RAM memory U5 is used for the storage and analysis of the digitized audible sounds. The address latch U3 latches the address from the CPU address/data bus during the first half of a memory access cycle.

The selection of peripherals which access the bus is done through an I/O - memory decoding process. The CPU can access 64 K bytes of memory and 256 I/O addresses. The address decoding logic chip U7 (part number 74HC139 available from National Semiconductor and other vendors) generates select lines to each peripheral on the bus. The logic is divided into two sections; the memory and the I/O selects. The following is a memory and I/O map of the respective peripherals:

| Ram Map | |
|---|---|
| 0000-7FFFH | PROM Memory |
| 8000-FFFFH | RAM Memory |
| I/O Map | |
| 20H | A/D Select |
| 40H | LCD Panel Interface Select |
| 60H | DAC AGC Select |
| 80H | I/O - Timer Select |

The CPU interface circuit U2 of FIG. 3b, attached to CPU U1 of FIG. 3a, is in the preferred embodiment party number NSC810 from National Semiconductor. This part is specially designed to operate with the NSC800 CPU to perform a plurality of timer, I/O and memory functions. There are 10 keys which operate the intelligent stethoscope, nine of which are configured in a 3×3 matrix which are driven by column and row I/O lines from the CPU interface circuit U2. One key (Power key) is configured as shown on the power control circuit and is used to activate initial power to the system. The other nine keys in the matrix perform the following functions:

| Key Name | Heart Mode Description |
|---|---|
| * Capture/ Continuous | Capture digitized waveform/or continuous real time display of received waveform. |
| * Enter | Enter captured waveform taken at 1 of 6 diagnostic locations. Diagnose heart sounds from 6 waveforms. |
| * Location | Increment location on the sternum display. |
| * Left pan | Pan left display of captured waveform. |
| * Right pan | Pan right display of captured waveform |
| * Expansion | Expand to X2, X5 horizontal display. |
| * Compression | Compress to X2, X1 horizontal display. |
| * Mode | Select mode of operation (Cardiac, Lungs, Bruits, etc.). |

The detailed electrical connections between the components shown in FIGS. 3a and 3b provide a microprocessor base on which the intelligent software will operate. The microprocessor, memory components and peripheral drivers and receivers operate both to control the functions of the stethoscope and to perform signal processing and signature analysis to analyze the heart sounds and to perform automatic diagnosis. Those skilled in the art will readily recognize many equivalents to the detailed electrical configurations shown in FIGS. 3a and 3b which illustrate only a preferred embodiment for the present invention.

Referring to FIG. 3d, the miniature microphone 225 is mounted in the bell 106 of the stethoscope where the sound pressure from the heart is picked up. The actual sound waves picked up by the chestpiece are passed intact to the physician's earpieces so that the user may hear the acoustic information just as it is received by the microphone of the intelligent stethoscope. The microphone used is not of a critical type and is of a common variety. The sensitivity of the microphone goes down to −65 dB referenced to 0 dB=1 v/ubar at 1 kHz. The output of the microphone is amplified and forwarded to the PCB assembly via a ground shielded cable. The audio heart sounds are DC biased to half the supply, then amplified by operational amplifier U15-3. The waveform is then passed through a low pass active filter utilizing operational amplifier U15-2, which will attenuate frequency components greater than 800 hz at a roll-off rate of 12 dB/octave. The filter functions as an antialiasing filter for the sampled data system which samples at a 3 Khz rate. The signal is then passed through 2 stages of high pass filter which will attenuate frequencies below 50 Hz at a rolloff rate of 24 dB/octave. All the filter are designed to have a maximally flat response with a Q=0.5. The five operational amplifiers U14-3, U14-2, U15-1, U15-2 and U15-3 are in the preferred embodiment part number LM324A available from National Semiconductor and other vendors.

The need for the gain control circuit comprised substantially of U13 and U14-3 is because the amplitude of heart sounds from various patients will vary. In order to perform valid waveform analysis, the amplitudes are scaled to nominal values. The digital gain control circuit will, under CPU control, automatically adjust the gain of the incoming cardiac sounds to conform to a preset nominal level. The digital gain is performed by implementing a digital to analog converter (DAC) (part number DAC0830 available from National Semiconductor and other vendors) in the feedback loop of operational amplifier U14-3. Gains of 1-256 can be realized by writing to the 8 bit input register of the DAC U13. The output of the digital automatic gain control circuit will always be adjusted so that peak heart sound S1 or S2 waveforms are at a nominal level.

The analog to digital conversion (A/D) is a process by which the conditioned heart sounds are digitized and stored in data base memory. Referring again to FIG. 3b, circuit U6 controlled by the CPU, performs the A/D function. This circuit is in the preferred embodiment part number ADC0801 available from National Semiconductor and other vendors. The audio waveform from the signal conditioning circuitry of FIG. 3d is sampled at a 3 kHz rate (every 333 us). The analog value is converted into an 8-bit digital equivalent and stored in RAM memory U5. In order to digitize a full cardiac cycle (max of 1.2 sec), 3600 samples are taken and stored at data base RAM memory U5 for future analysis.

The A/D converter U6 accepts inputs from between 0-5 V. In the preferred embodiment, a 2.5 V baseline is used and the A/D converter accepts ±2.5 V signals. A precision voltage reference U12 (part number LM336 from National Semiconductor) is used to reference the incoming analog signal to a full scale input. The CPU U1 writes to the A/D converter U6 to initiate the conversion process. When the conversion is complete, U6 interrupts the CPU U1 and the data is read from the data bus and written into memory U5.

The LCD panel interface shown in FIG. 3c is an intelligent controller which coordinates the functions and generate the signals necessary to drive an LCD graphics panel. The interface circuit U10 is connected to the CPU data bus and control signals and is in the preferred embodiment part number HD61830B available from Hitachi Semiconductor. In conjunction with the interface is a CMOS memory circuit U11 which contains the data which is currently being displayed on the LCD panel 102. The LCD panel 102 is autonomously refreshed from the signals generated by the interface circuit and the data patterns stored in RAM memory U11. The display changes by the CPU directing a set of commands to the interface circuit and modifying the display RAM memory, and in turn the display.

The LCD dot matrix graphics display panel 102 is part number DMF612 available from Optrex Corp. and is made up of dots or pixels (0.41 mm square). The matrix is configured as 64 vertical × 480 horizontal dot resolution. The panel will display graphic cardiac waveforms along with alphanumeric characters during the procedures for waveform capture and diagnoses.

The intelligent stethoscope system also has a four wire interface for serial communication to dedicated peripherals shown in FIG. 3b. These peripherals would be used for plotting cardiac waveforms, or storage of the waveform data base memory for future retrieval. The I/O interface circuit U2 of FIG. 3b uses its programmable I/O lines to generate two output lines and one input line for the peripheral interface. The following lines are used in the peripheral interface:

| * Data Input | * Clock |
|---|---|
| * Data Output | * Ground |

Software Description

The software, programmed to run on the CPU 207 and held in memory 217, can be divided into two major sections. The first is the software which drives the hardware and performs the actual operation of the intelligent stethoscope. The first section is detailed in the flow diagram entitled operational flow and described in FIGS. 4a-4c. Reference to the hardware schematics (FIGS. 3a-3e) should also be made while reading the following description of the operational flow. The second section performs diagnosis of the captured cardiac waveforms through a process of waveform signature analysis and is described in great detail in conjunction with FIGS. 8a-8g.

Just as normal heart sounds have a signature, all cardiac murmurs have a unique signature. The signature or unique waveform generated by these murmurs are directly related to an anatomic abnormality of the heart. Through unique waveform signature analysis procedures of the present invention used in conjunction with the medical diagnostic matrices and algorithms described herein, the present invention is able to identify the audible characteristics of cardiac sounds and determine the presence or absence of a murmur. In addition, the intelligent stethoscope of the present invention can specifically determine which type of murmur is present and its relative intensity.

The following text details the signature analysis procedures and the medical matrix diagnostic algorithm for the murmur of Mitral Stenosis. This murmur has been chosen for detailed analysis because of its relative complexity and extensive use of waveform signature analysis techniques. The following text also outlines the unique characteristics of all the murmurs which the instrument will detect, and uses the same diagnostic procedures for determining their presence. The following text also outlines the techniques used for generating matrices to allow the preferred embodiment of the present invention to do automatic diagnosis of other body sounds such as lung sounds, vascular sounds, etc.

Those skilled in the art will readily recognize the application of the present invention along with the algorithms used for performing the diagnostic signature analysis to a wide variety of auscultation techniques. The present invention is described in terms of a preferred embodiment and the matrices are described in terms of heart and lung sounds to show a preferred implementation and to teach one skilled in the art how to practice the invention. It will be readily apparent, however, that the present invention is not merely limited to cardiac or lung sounds. With the teachings of the present invention, one skilled in the medical arts will readily recognize how to generate the appropriate matrices for the diagnosis of a wide variety of ailments based on auscultation. A few examples of the matrices used by the present invention to diagnose abnormalities are given but are no means exhaustive.

Operational Flow

Figure 4A:
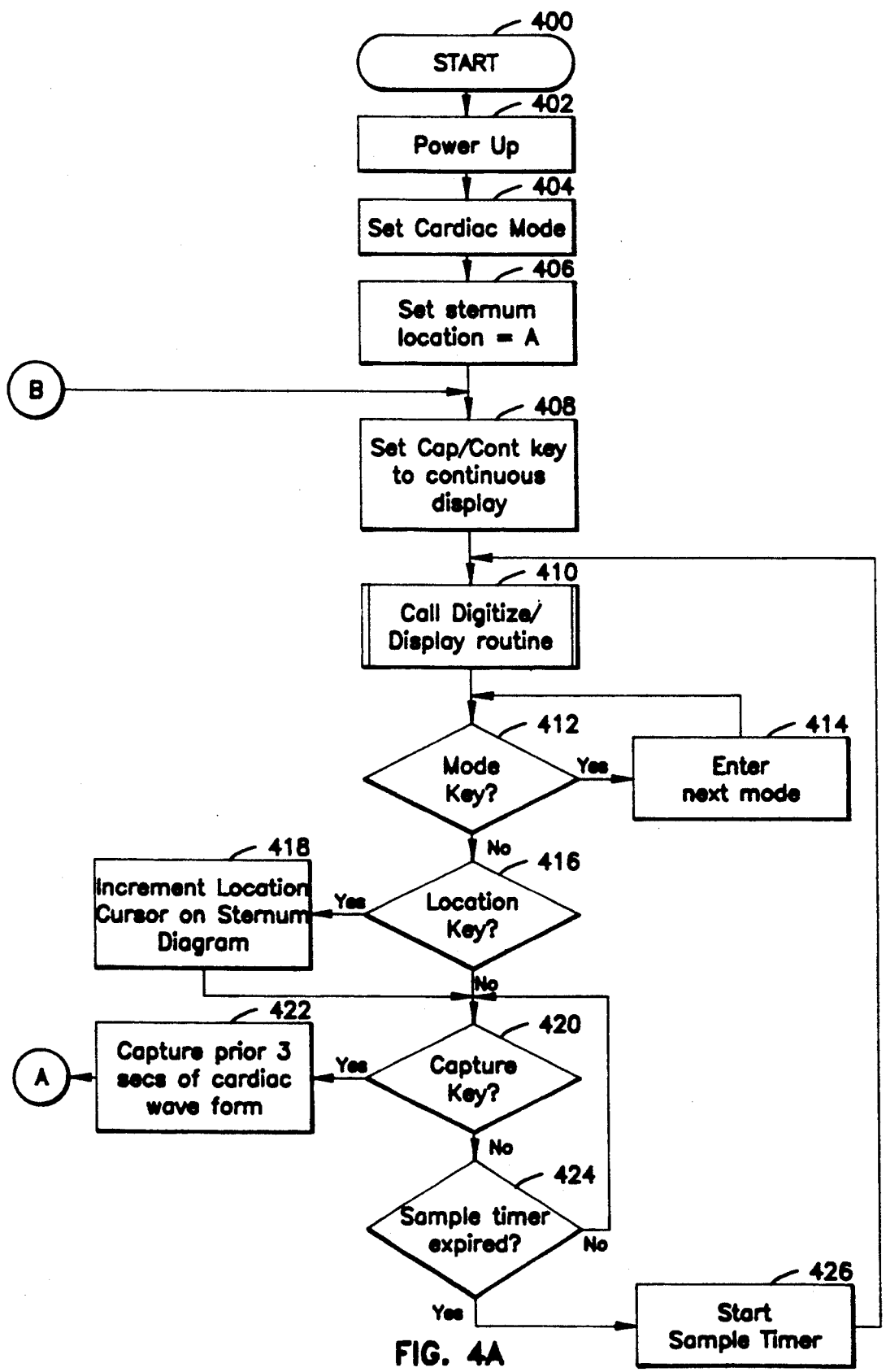
FIGS. 4a, 4b and 4c are detailed software flow charts representing the operational flow of the intelligent stethoscope.
Figure 4B:
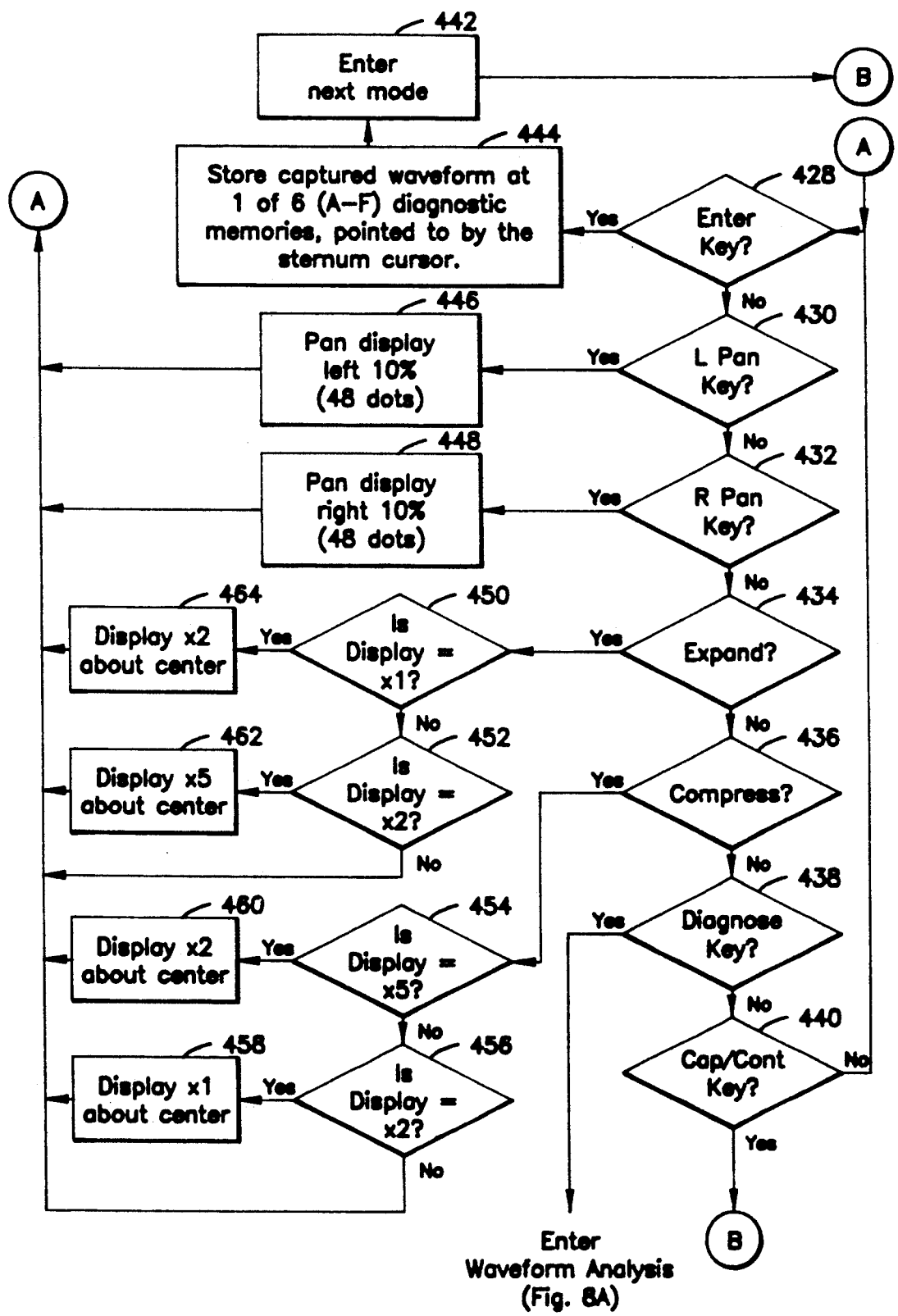
Figure 4C:
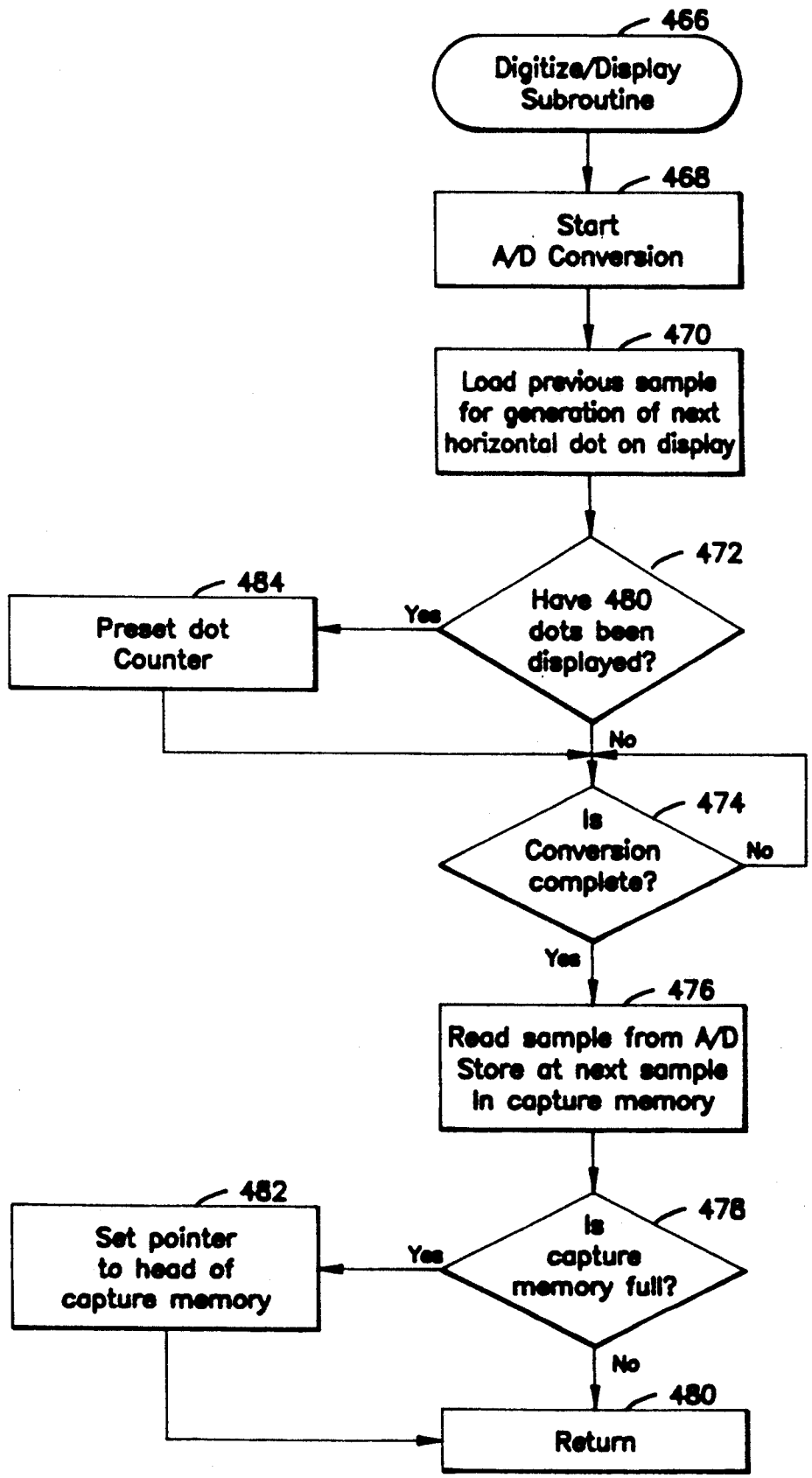

The operational flow and housekeeping duties performed by the microprocessor in the preferred embodiment of the present invention are described in FIGS. 4a-4c. Reference to electrical schematic diagrams 3a-3e invention.

The main control flow begins on FIG. 4a in box 400. The system is powered up at box 402 by a momentary closure of the power switch. The mode of operation is defaulted to cardiac mode in box 404 for convenience. Other modes of operation may be the default mode. The display indicates the location on the sternum to begin auscultation in box 406. The microprocessor also defaults to a continuous display instead of a capture display as shown in box 408. At this point in the operational flow, the "Digitize/Display" subroutine is called at location 410 (described in FIG. 4c). Once a waveform sample is digitized, stored in memory and displayed as the next dot on the LCD display, the various operational keys are polled to determine the next step. For example, at location 412 the mode key is polled to test whether the next mode of operation should be entered at location 414. If the location key is pressed as shown in decision box 416, the location cursor on the sternum diagram on the display is incremented to show the physician the next location to probe for receiving auscultation sounds. If the Capture key was pressed, as shown in decision box 420, the last three seconds of the cardiac waveform is captured as shown in box 422. This loop is repeated out of decision box 424 until the sample timer has expired, allowing the program control flow to enter box 426 where a sample timer is restarted and the next sample is taken.

Additional control flow is shown in FIG. 4b. The keys are continued to be polled by the microprocessor to test for additional control operations. Control passes from FIG. 4a through the continuation bubble A to decision box 428 where the keyboard is polled to determine whether the Enter key has been pressed. In order to poll the keys on the keyboard, decision boxes 428 through 440 comprise a polling control flow to check the status of the keys. The Pan Left key is polled by decision box 430, the Pan Right key is polled by decision box 432, the Expand key is polled by decision box 434, the Compress key is polled by decision box 436, the Diagnose key is polled by decision box 438, and the Capture or Continuous Display key is polled by decision box 440. The control loop is continued from decision box 440 to decision box 428 in a loop to continually poll the keyboard to determine whether any of the keys have been pressed.

If the Enter key has been pressed, control is passed from decision box 428 to box 444 where the captured waveform is stored in one of the six diagnostic memories in order to begin building the diagnostic matrix for later diagnosis of the sounds. Flow is passed through decision box 442 where the display is incremented so that the new sternum position of the acoustic bell is indicated to the physician and control is passed back through bubble B to FIG. 4a to begin the loop to capture more data at decision box 408.

If the Pan Left key or the Pan Right key are pressed on the keyboard, control is passed from decision box 430 to decision box 446 or decision box 432 to decision box 448 respectively. These keys control the display of the captured waveform and allow the waveform to be panned on the display to view the previous cardiac cycles captured in memory. By allowing the panning function, up to four cardiac cycles (depending upon the patient's heart rate) may be viewed by moving it left or right.

The display can also be manipulated to expand the cardiac waveform by pressing the Expand key. The Expand command out of decision box 434 enters decision box 450 where the amount of expansion is polled. Decision box 450 determines whether the display is currently at normal size. If it is, the display is expanded by 2 in command box 464. If the display has already been expanded, control passes from decision box 450 to decision box 452 where it is polled whether the display has already been expanded by 2. If it has, the display is then expanded by 5 in command box 462. However, if the display has already been expanded by 5, continuous pressing of the Expand key will pass control out of decision box 452 along the "No" line and return control to bubble A of FIG. 4a.

In a like fashion, the display can be compressed back to its normal size to in effect back out the Expand feature. If the Compress key is pressed, control passes from decision box 436 to decision box 454 where it is tested whether the display has been expanded to 5 times its original size. If so, the display is compressed down to 2 times its original size in command box 460. If the display has not been expanded to 5 times its original size, control is passed from decision box 454 to decision box 456 where it is checked whether the display has been expanded to twice its size. If not, control is passed to bubble A in FIG. 4a since continual pressing of the Compress key will do nothing. If, however, the display is currently at twice its original size due to the Expand key, control is passed from decision box 456 to command box 458 where the display is set to normal size. Control from all of these decisions is passed back to bubble A in FIG. 4a.

If the Diagnose key is pressed, control is passed from decision box 438 to the waveform analysis and diagnostic routines described in detail below. Software for performing the waveform signature analysis and performing the diagnosis comprise the second section of software and provide the intelligence of the present invention.

Referring once again to FIG. 4a, the Digitize/Display subroutine called from location 410 performs the function of capturing the heart sounds, digitally encoding and storing them in memory and displaying the analog representation on the display. This subroutine is described in detail in FIG. 4c. Control enters Digitize/Display subroutine at location 466. Command box 468 commences the analog-to-digital conversion process under microprocessor control and timing. As each digital sample from the A-to-D converter is received, it is used by the display driver to generate the dots on the display as shown in command box 470. Decision box 472 determines whether 480 dots along the horizontal axis have been displayed on the LCD display. If 480 dots have been displayed, the dot counter is preset by command box 484 and control is passed to decision box 474. At this location, a tight loop is performed until the A-to-D conversion is complete. This tight loop is necessary since the display of the previously loaded data can often be completed before the A-to-D conversion for the particular sample may be completed. Thus, decision box 474 and its associated tight loop ensures that subsequent processing is delayed until the completion of both A-to-D conversion and display functions.

Once the A-to-D conversion process is complete, control is passed to command box 476 where the just-completed sample is loaded into the capture memory for display while the next sample is converted by the A-to-D converter. Control is then passed to decision box 478 where the capture memory is checked to determine if it is full. If so, control is passed to command box 482 where the pointer into the capture memory is reset to the head. Regardless of the status of the capture memory, however, control is passed back through return box 480 to the main calling routine shown in FIG. 4a.

This completes the detailed description of the first section of software which controls the actual operation of the intelligent stethoscope. Once the appropriate digitized audio samples taken from the various body locations have been stored in memory, the next step is to diagnose the stored data and give the results of the diagnosis to the physician via the display. Thus, the waveform signature analysis, described in detail below, is performed wholly within the microprocessor and its associated memory and does not require the assistance of the peripheral hardware of the intelligent stethoscope. Those skilled in the art will readily recognize, therefore, that the diagnostic routines may not actually be completed within the intelligent stethoscope, but may be downloaded into a co-processor at another physical location to complete the diagnosis. Where the actual diagnostic steps and waveform signature analysis is performed is irrelevant to the invention described herein. It is only within the preferred embodiment of the present invention that the diagnosis of the stored digitized audio patterns is performed within the intelligent stethoscope.

Waveform Signature Analysis

All of the waveform signature analysis procedures are performed after the conditioned audio signals have been digitized. Therefore, digital signal processing procedures are used in determining the unique waveform characteristics of each murmur. The digital waveform analysis is a complex and time consuming process, but need not be performed on a real time basis. All necessary waveforms are digitized and stored in waveform memory 219. Then, upon command, the waveform signature analysis and medical diagnostic algorithms are performed. Depending on which murmur is present and the speed of microprocessors employed in the design, this process may take up to several seconds to complete.

The software flow diagrams described below are drawn at a sufficiently detailed level to enable one skilled in the art to program the algorithms into a microprocessor-based intelligent stethoscope. The flow diagrams are intended to teach at a quite detailed level the algorithms used and the steps required to perform the analysis. The digital waveform analysis performed by the software includes many techniques well known to those skilled in the digital arts to which the software portion of the present invention pertains. Although specific techniques are described for performing a variety of digital signal processing steps, those skilled in the art will readily recognize the availability of substitute methods and techniques for performing the same result in an equivalent fashion. As those skilled in the art will readily admit, a wide variety of alternatives are available to the programmer of a microprocessor-based design to achieve the same results. Therefore, the following software description is exemplary of the preferred embodiment but is not intended to limit the present invention to a specific software flow for accomplishing this result.

In the waveform signature analysis detection procedures of cardiac murmurs, five general waveform characteristics must be identified:

A. Amplitude

The amplitude is the intensity of the sound pressure measured at each sample of the audio waveform. The instantaneous amplitude is measured by an 8-bit value derived from the analog to digital conversion process.

B. Time

Time intervals and waveform timing are derived from the summation of digitized samples. Each point on the waveform is sampled, in the preferred embodiment, every 333 microseconds, therefore 3600 samples are taken over a 1.2-second cardiac cycle.

C. Frequency

Frequency is defined as the inverse function of the period of a waveform. The period can be determined by the point of alternate zero crossing of a periodic waveform. Therefore, the frequency of an impulse or a periodic waveform can be determined by the time duration or number of samples between alternate zero crossings.

D. Peak Amplitudes

Peak amplitudes are detected as the point of maximum amplitude taken over a defined period of time.

E. Spectral Power Density

The parameter of spectral power density is a measurement of signal energy and major frequency component for a selected period of time. This parameter is obtained using the previously defined functions of amplitude, frequency, and time interval. This parameter is used in analyzing waveform components which can indicate the intensity and pitch of a murmur during defined time intervals of systole or diastole.

The sounds to be digitized, stored and analyzed are various types of body sounds. In the preferred embodiment of the present invention, heart sounds are analyzed to determine heart abnormalities. Also described below is the analysis and diagnosis of lung sounds and cardiovascular sounds. For purposes of the software description, however, we will concentrate on describing heart sounds.

Heart sounds result from vibrations associated with the sudden closure of heart valves and the acceleration and deacceleration of adjacent blood flow. These vibrations are transmitted to the body surface and are heard as heart sounds. Usually heard at the apex, the first heart sound (S1) is associated with tricuspid and mitral valve closures. Because the mitral valve usually closes before the tricuspid, the sound splits into two components. The second heart sound (S2) is associated with aortic and pulmonic valve closures. Physiologic splitting of S2 results when the pulmonic valve closes later than the aortic during inspiration. The aortic component is normally much louder than the pulmonic component.

Murmurs are sounds resulting from turbulent blood flow in the heart and are characterized by a variety of qualities of sound (described in more detail below).

Figure 5:
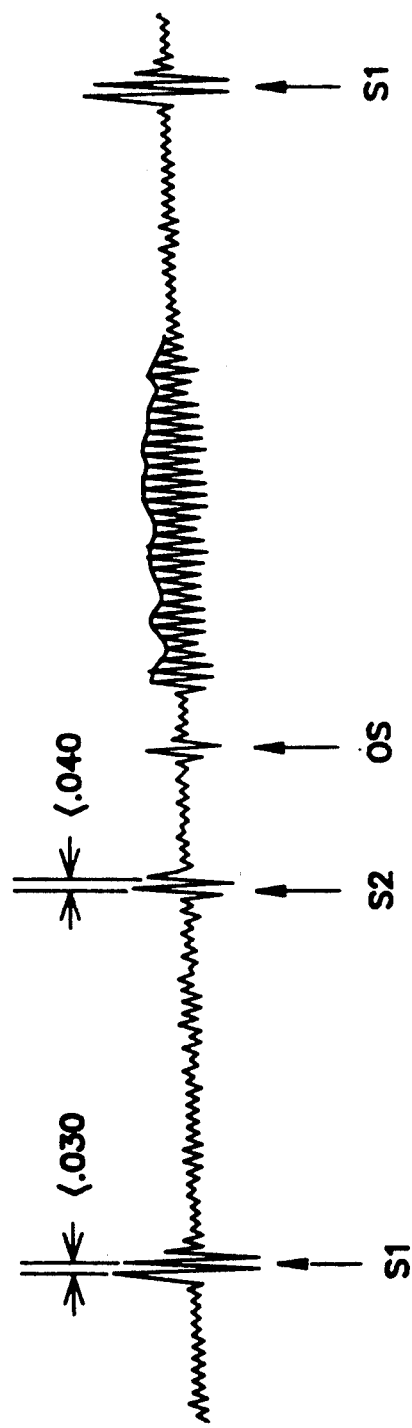
FIG. 5 shows a detailed wave form typical of the murmur from a heart suffering from mitral stenosis.

The determining factor which distinguishes the first heart sound (S1) from the second heart sound (S2) is the percentage of time of diastole to systole of the full cardiac cycle. Using FIG. 5 as a guide, the systolic period of a cardiac cycle starts with S1 heart sounds and lasts for about one-third of a full cardiac cycle. S2 heart sounds are then generated which is followed by the diastolic period. The diastolic period lasts for about two-thirds, or the remainder, of the cardiac cycle.

The use of peak amplitude method of waveform analysis is employed to determine the location of three successive heart sounds. By using time interval analysis, we can determine the periods of systole and diastole and therefore can record the addresses (i.e., locations within the cardiac cycle) of S1 and S2.

According to the defined medical matrix described in detail below, the determination of normal or abnormal splitting of heart sounds S1 and S2 must be made. The first component of heart sound S1 is made up of the closing of the mitral valve followed by the tricuspid valve. The first component of the second heart sound S2 is made up of the closure of the aortic valve followed by the pulmonic valve. The time between the splitting of the valves at S1 should be <0.30 sec and the splitting at S2 should be <0.040 sec.

In the waveform analysis, the microprocessor points to the first peak of S1 which was previously detected. Using the peak analysis method, the microprocessor then determine the next peak within a 10% (120 ms)

window. Upon determining the closing point of the second valve of S1, a time measurement is made using the time interval analysis between the two valve sounds of S1. If the time between the peaks generated by the two valve sounds is more than 0.030 secs, then a condition of abnormal splitting exists. The same analysis takes place for the determination of abnormal splitting of S2 valve closures. The maximum limit for splitting for S2 is 0.040 seconds. The results of the splitting of S1 and S2 are then generated on the diagnostic matrix (described below).

In the detection of systolic or diastolic murmurs, the analysis is the same except for the time interval which is being examined. Systolic murmurs are present during the period of systole. Diastolic murmurs, are present during the period of diastole. The microprocessor software routines look for murmurs which manifest themselves as spectral energy with frequency components in the range of 70–500 Hz. The energy level correlates with the intensity of the murmur. The major components of frequency define the pitch of the murmur. The analysis of these murmurs utilizes the concept of spectral power density which was previously defined as a measurement of signal energy and major frequency spectrum for a selected time interval.

Initially a time interval is established in which to examine the heart sounds. The time intervals are mid-, pre-, and early diastolic and systolic. From the measured peak amplitudes, and using a linear predictive interpolation method between the peaks, we can create a power (energy) envelope for the selected time interval (see FIG. 5). At each sample during the interval, there will be defined a point on this power envelope. The area under the power envelope curve shall be integrated by a summation of the area at each sample. The total area under the curve shall indicate the energy level of the murmur. The murmur energy is then quantized into three levels: faint, moderate, and intense.

The analysis also includes the frequency range of the murmur. Generally a murmur waveform will be made up of many frequency components. The objective is to determine the frequency component which makes up the majority of the energy under the power envelope.

The period of the peak waveforms reaching a defined threshold are averaged over the time interval under observation. The inverse function is performed on the average period to obtain the average frequency under the power envelope. The major frequency component under the power curve is also quantized into three levels: 70–120 Hz is low pitched, 120–250 Hz is medium pitched, and 250–500 Hz is high pitched. These levels are also termed rumbling, rough, and blowing.

There also exists a relationship between the degree of stenosis within a heart valve and the major frequency component of a murmur at its peak amplitude. An alternate embodiment of the present invention includes the ability to determine the actual diameter of a stenotic valve. Those skilled in the art will recognize upon reading and understanding the present description of the preferred embodiment of the present invention that the frequency spectrum of a specific time interval of the murmur can be analyzed through the process of fast fourier transforms to determine this diameter and degree of stenosis.

Murmurs or abnormal heart sounds are noises generated by the flow of blood through the heart. The frequency range of most heart murmurs varies between about 70 to 460 cps. Rumbling or low pitched murmurs fall into the 70 to 110 cps range. Murmurs in the 120 to 250 cps range are classified as rough murmurs of faint to moderate intensity. Frequencies of 300 cps or greater are considered high frequencies and blowing. When a murmur consists of a narrow band of frequencies it may be described as musical, and when it consists of a broad range of frequencies it is usually described as harsh. For the purpose of this detailed description of the preferred embodiment, "murmurs" will be used to describe all abnormal heart sounds, including clicks, snaps, etc.

The key elements used in the preferred embodiment of the present invention in diagnosing heart murmurs are:

1) Timing of the murmur (systolic or diastolic).
2) The point of maximum intensity (the location on the chest wall of maximum intensity or loudness).
3) The pitch and quality of the sounds.
4) Finer timing (the location in either systole or diastole).
5) Other unique sounds and their respective locations on the chest wall associated with specific heart murmurs.

It is appropriate to note that the human ear hears frequencies in the 500 to 3000 cps range well, but hears frequencies below 500 cps poorly and frequencies below 300 cps very poorly. The present invention does not have this low range frequency difficulty.

In the heart mode, the stethoscope chest piece is applied to the chest wall in six specific locations according to a diagram 601 on the display 102. The locations are (see FIG. 6):

| | | |
|---|---|---|
| 1) | Right second intercostal space | (A) |
| 2) | Left second intercostal space | (B) |
| 3) | Left third intercostal space | (C) |
| 4) | Left fourth intercostal space | (D) |
| 5) | Left fifth intercostal space | (E) |
| 6) | The apex (F) 602 | |

The sixth position at the apex 602 will be located by listening for the point of maximum intensity (PMI) through the area of the apex, i.e. from the lower left sternal border to the left anterior axillary line, and by visual determination of the waveform of greatest magnitude on the display as the chest piece is moved through the area of the apex. A specific order of auscultation will be followed when obtaining the six locations by observing the location of a marker on the LCD sternal diagram 601 which will constantly illustrate the location to obtain next.

Confirmation that a good signal is obtained in each of the six locations will be obtained by visualizing the waveform on the display simultaneously while listening to the audible signal through the earpieces. When the user has confirmed a good signal is obtained the "capture" button is pushed, which will freeze the waveform on the display. The user can then visually inspect the waveform before sending it to memory by pressing the "enter" button. If a poor quality waveform is recorded inadvertently the user will be able to record a substitute waveform from a location by moving a cursor to the desired location on the LCD sternal diagram 601 and repeating the recording for that location.

The software for controlling the digitizing and storing of the heart sounds (described above) is designed to make eight determinations of the waveform pattern obtained at each of the six locations on the chest wall as well as determine the point(s) of maximum intensity by comparative analysis of all six waveforms. The eight determinations are:
1) Does a first heart sound (S1) exist?
2) Does a second heart sound (S2) exist?
3) Is the first heart sound normally split?
4) Is the second heart sound normally split?
5) Is there a systolic murmur?
6) Is there a diastolic murmur?
7) Is the first heart sound greater than the second heart sound?
8) Is the first heart sound equal to the second heart sound?

Figure 6:
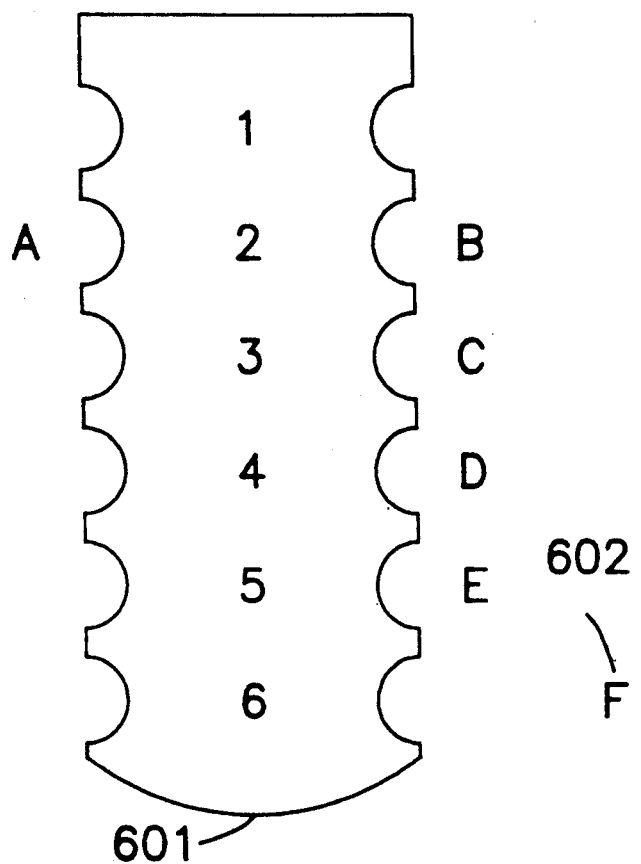
FIG. 6 is a closeup view of the display of the intelligent stethoscope which directs the seven chest wall locations to be recorded.

A comparative analysis process will be performed by constructing a data matrix (701, 702, etc.) incorporating the six locations on the chest wall with the eight determinations of the waveform patterns obtained at each location as well as the PMI (see FIG. 6). The overall PMI(s) will be determined by computer analysis of the largest amplitudes of all six waveforms. Specific matrices represent normal (701) or abnormal (702, etc.) waveform patterns. Abnormal waveforms determined by individual matrices are further evaluated by specific algorithms. The algorithms utilize frequency, timing, and amplitude criteria to yield diagnostic information to the user.

Specific operating instructions are shown on the liquid crystal display at particular algorithm locations when user input is necessary to proceed with an algorithm determination. An example of how the instrument detects a heart murmur is described in detail below for mitral stenosis. In addition, the preferred embodiment of the present invention is able to detect the following heart sounds which are described in detail later in the text:
1) Normal heart sounds
2) Various abnormal and extra heart sounds
3) Mitral regurgitation (see FIG. 9c)
4) Mitral valve prolapse
5) Tricuspid stenosis (see FIG. 9d)
6) Tricuspid regurgitation
7) Various types of aortic stenosis (see FIG. 9a)
8) Aortic regurgitation (see FIG. 9b)
9) Atrial septal defect
10) Ventricular septal defect
11) Patent ductus arteriosus
12) Tetralogy of fallot
13) Innocent systolic murmurs
14) Pulmonary hypertension
15) Systemic hypertension and arteriosclerosis
16) Coarctation of the aorta
17) Pulmonary regurgitation
18) Pericardial friction rub
19) Cardiac arrhythmias
20) Pulmonary valvular stenosis with an intact ventricular septum
21) Postsurgical sounds
22) Acute rheumatic carditis
23) Acute myocardial ischemia and infarction
24) Auscultatory sounds in various conditions

Example of Determination of Murmur of Mitral Stenosis

The murmur of mitral stenosis is produced by the flow of blood into the left ventricle during diastole. Because of the stenotic valve the filling of the ventricle is slower, therefore mitral stenosis is associated with an accentuated first heart sound. When the first heart sound is loud, there is usually an opening snap of the mitral valve (see FIG. 5).

The earliest murmur of mitral stenosis is nearly always a mid-diastolic murmur. Toward the end of diastole, further narrowing of the mitral orifice, associated with an increase in blood flow produced by atrial contraction, results in a presystolic murmur and is crescendo in quality, ending in the first heart sound. As the degree of stenosis increases, the mid-diastolic and presystolic murmurs fuse together.

The murmur of mitral stenosis is maximum at the apex and is generally confined to a small area on the chest wall. This area is sometimes located more laterally and posteriorly when the right ventricle is enlarged. The murmur is low pitched but can become rough when loud. The murmur is either unchanged by respiration or diminished by inspiration. By following the normal operations protocol of the instrument, the chest piece is moved to each of the six locations on the chest wall as outlined above. From the six waveform patterns the following matrix is obtained:

|     | A   | B   | C   | D   | E   | F   |
| --- | --- | --- | --- | --- | --- | --- |
| PMI |     |     |     |     |     | X   |
| 1   | Y   | Y   | Y   | Y   | Y   | Y   |
| 2   | Y   | Y   | Y   | Y   | Y   | Y   |
| 3   | Y   | Y   | Y   | Y   | Y   | Y   |
| 4   | Y   | Y   | Y   | Y   | Y   | Y   |
| 5   | N   | N   | N   | N   | N   | N   |
| 6   | Y/N | Y/N | Y/N | Y/N | Y/N | Y   |
| 7   | Y/N | Y/N | Y/N | Y/N | Y/N | Y   |
| 8   | Y/N | Y/N | Y/N | Y/N | Y/N | N   |

(A-F correspond to the six locations on the chest wall.)

This matrix is then identified as possible mitral stenosis (as described below) and the appropriate detailed diagnostic algorithm (also described below) is commenced. The above matrix translates to a PMI at the apex:
1) A first heart sound exists
2) A second heart sound exists
3) S1 is normally split
4) S2 is normally split
5) No systolic murmur is present
6) A diastolic murmur is present at the apex and possibly higher up the sternum
7) S1 is greater than S2 at the apex
8) S1 is not equal to S2 at the apex but may be equal higher up the sternum The first determination in the detailed Mitral Stenosis Diagnostic Algorithm (FIGS. 8f-8g described below) is if the murmur is increased in magnitude with inspiration. This is obtained by displaying a message to the user to have the patient inhale while the chestpiece is held at the PMI. If the software determines that the murmur is increased in magnitude by comparative analysis to the previous PMI held in memory, then the detailed diagnostic algorithm for tricuspid stenosis is commenced. If the murmur is either unchanged or decreased by inspiration the same algorithm is continued and the next determination, early diastolic murmur, is performed.

If an early diastolic murmur is detected, the next determination will be a mid-diastolic murmur. If an early diastolic murmur is not detected, a different path in the algorithm will be commenced. In each position of the appropriate algorithm a determination is made based on the frequency and timing of the waveform pattern obtained from the PMI in memory. Diagnostic information of mitral stenosis is therefore derived from the algorithm identifications. Combinations of valvular lesions such as mitral stenosis occurring in conjunction with mitral regurgitation will be identified by matrix/algorithm sequences based on the PMI's, frequency and timing the murmurs.

Diagnostic Software

The foregoing description of the generation of the matrices from the received heart sounds and the diagnosis therefrom is performed under software control within the microprocessor and memory of the preferred embodiment of the present invention. A detailed flow chart describing the algorithm for analyzing the heart sounds is described in FIGS. 8a-8e. A detailed diagnostic algorithm for mitral stenosis is described in detail in FIGS. 8f and 8g. The detailed algorithms described below are exemplary of the preferred embodiment of the present invention and although they describe a specific diagnostic technique for determining mitral stenosis, they are not intended to be limiting only to mitral stenosis but are only intended to show the application of the present invention to the diagnosis of a wide variety of heart, lung, cardiovascular, etc., abnormalities through the automatic diagnosis using the present invention. Those skilled in the art will readily recognize the application of the software algorithms and the technique of using the matrices for diagnosis, to the diagnosis of a wide variety of ailments through the use of auscultation.

Figure 8A:
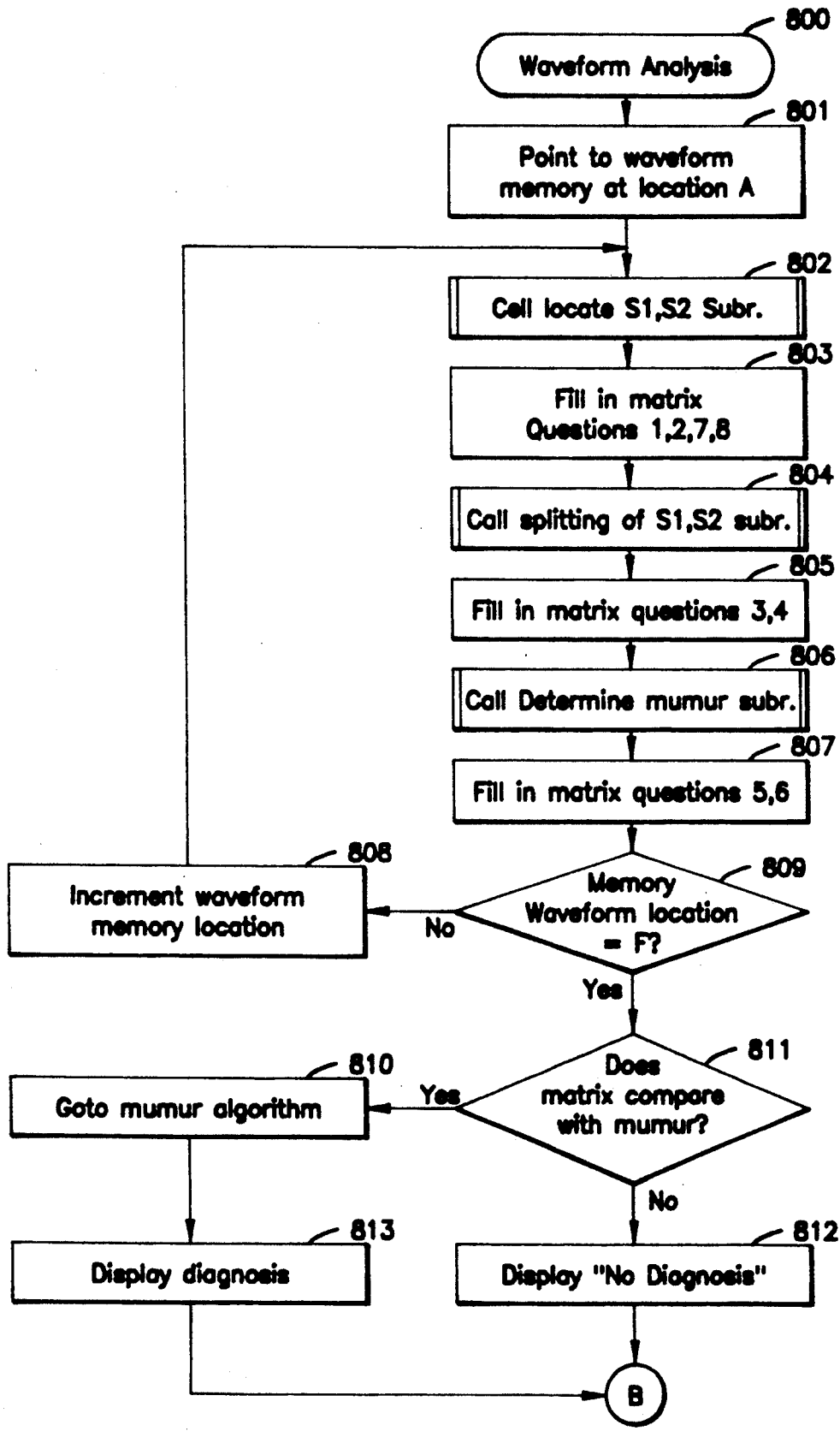

Referring to FIG. 8a, the waveform analysis entry into the software at control box 800 was previously called under software control from decision box 438 in FIG. 4b. The diagnosis routines are initiated by the pressing of the Diagnose key. Control is immediately passed to command box 801 which initializes a pointer into waveform memory for location A representing the signals obtained from location A on the sternum diagram (shown in FIG. 6). Control is passed to command box 802 where the subroutine "Locate S1 and S2" is called. This subroutine (found in FIG. 8b and described in more detail below) determines the locations of the S1 and S2 heart sounds within the sampled cardiac waveform. Using the information obtained from the subroutine, control is passed to command box 803 where matrix questions 1, 2, 7 and 8 are filled in based on this information. Referring back to FIG. 7, these questions correspond to whether the S1 and S2 sounds exist and whether the S1 sound is greater than S2 or equal to S2.

Control at this point is passed to command box 804, where the subroutine "Splitting of S1 and S2" is called (shown in FIG. 8d and described in more detail below). Control is then passed to command box 805 where the information obtained from the aforementioned subroutine is used to fill in matrix questions 3 and 4. Referring briefly to FIG. 7, these questions correspond to whether S1 and S2 are normally split.

Control at this point is passed to the "Determine" subroutine at command box 806. The "Determine" subroutine of command box 806 (described in detail below and shown in FIG. 8e) returns information regarding the systolic or diastolic murmurs. This information is calculated and control is passed to command box 807 which fills in the remaining questions 5 and 6 of the matrix to complete the matrix. Referring briefly to FIG. 7, questions 5 and 6 determine whether there is a systolic or diastolic murmur.

The matrix being complete, control is passed to decision box 809 to determine whether all seven of the waveform locations have been loaded in the matrix. If the memory waveform is not equal to F (indicating the end of the complete matrix), control is passed to command box 808 which increments the waveform memory location. Hence, if the microprocessor has just completed waveform memory location A corresponding to column A of matrix 701 shown in FIG. 7, the program would increment to column B corresponding to the left second intercostal space for answering the seven questions from this new location as shown in FIG. 7.

Once the entire matrix is filled in, control is passed to decision box 811 in which the generated matrix is compared against a plurality of stored matrices corresponding to a variety of heart abnormalities. As described above, the stored matrices may correspond to, for example, mitral stenosis, mitral regurgitation, tricuspid stenosis, aortic regurgitation, etc. A non-exhaustive list of heart ailments that can be diagnosed using the preferred embodiment of the present invention has been previously given above, and such ailments are described in detail below. All the matrices for determining these heart ailments are not given, for reasons of brevity and clarity; however, those skilled in the art will readily recognize from the descriptions contained within the present patent application the matrices are readily identifiable. In addition to the ailments described within the present patent application, a wide variety of other heart ailments fit the pattern described herein for diagnosing said ailments, and the matrices corresponding thereto can be readily generated. An additional number of matrices corresponding to several heart abnormalities are given and described below.

In addition to the matrices described herein, and in addition to the heart ailments readily diagnosed by the present invention and described herein, a wide variety of other ailments may be diagnosed by the present invention by generating matrices corresponding to other ailments by means of auscultation for lung sounds, cardiovascular sounds, bruits, etc.

Referring once again to FIG. 8A, if the generated matrix from the received heart sounds do not match any of the matrices contained in memory corresponding to known heart ailments, control is passed to command box 812 which indicates on the LCD display a "no diagnosis" symbol indicating that a matrix mismatch has occurred. In this event, control is passed via continuation bubble B to FIG. 4A in which the hardware is reset for regenerating a matrix by means of inputting new data from the beginning.

Assuming however that a matrix match does occur from decision box 811, control is passed to control box 810 in which the detailed diagnostic algorithm where the specific diagnosis is invoked. Thus in the example described below, the received data and the algorithm generated therefrom correspond to mitral stenosis and hence location 810 corresponds to calling the diagnostic algorithm for mitral stenosis. These detailed algorithms, described in more detail below, are necessary for determining the type and severity of the specific heart ailments uncovered by the matrix matching. As in the case of mitral stenosis, a wide variety of types of mitral stenosis may be indicated. Once the specific diagnosis of the type of mitral stenosis has been determined, or if the specific type of any indicated heart ailment has been determined from the murmur algorithm called from location 810, control is passed to command box 813 where the actual diagnosis determined is displayed. Control is then returned back to the main control via continuation bubble B to FIG. 4A.

Figure 8C:
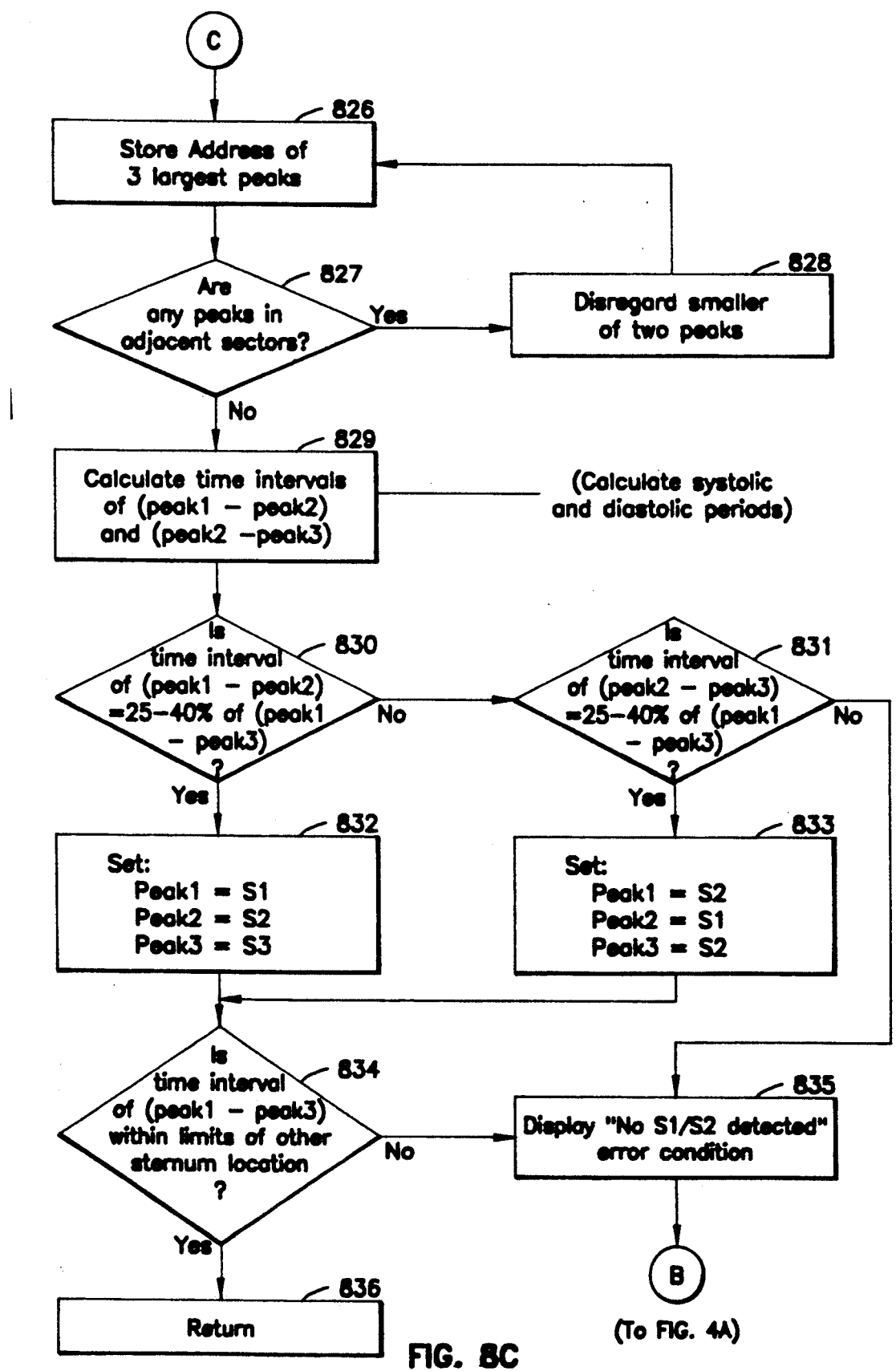

The subroutine to locate S1 and S2 within the cardiac waveform is described in detail in FIG. 8B and 8C. Control is passed through entry point 815 to command box 816 in which the pointer in the waveform memory is positioned at the head of the memory to initialize the memory pointer. Control passing to command box 817 presets the section counter to 10. Each section is 120 milliseconds, since a typical cardiac waveform is less than 1.2 seconds in duration and is divided into 10 sections. Control is then passed within the major loop for determining the data within each section. Control passing to command box 818 presets the sample counter to 360. Each section contains 360 samples of a waveform and hence when the sample count reaches zero, the analysis for the particular section is complete. Control enters the decision box 820 which checks whether a zero crossing of the waveform has been found. Once a zero crossing is encountered, the peak for this particular excursion from zero is calculated to determine whether it is the largest in the section or sector in decision box 821. If this is the largest yet encountered excursion from zero, this data is recorded as the peak value within the section at command 822.

Regardless of whether the peak determined is the largest or less than the largest peak within this sector, control is passed to decision box 819 where the sample count within the section is checked to determine whether it has reached 0. As was previously described, when the sample count within a particular section reaches 0, the entire section has been analyzed for the peak value. If the sample count does not reach 0, the internal minor loop passes control back to decision 820 to continue searching for the largest peak in this sector. If this sector has been analyzed, control is passed to control box 823 where the address of the peak value for the selected sector is recorded. Command is then passed to decision box 824 where the sector count is decremented to begin looking for the peak value within the next sector. Decision box 824 therefore completes the major loop for looping through the ten sectors of the display as shown in FIG. 8B. Once the sector counter reaches 0, all the peak values for all ten sectors have been calculated and stored and control is passed via continuation bubble C to FIG. 8C.

Referring to FIG. 8C, control is passed to command box 826 where the addresses of the three largest peaks determined above are stored. Control is then passed to decision box 827 where any of the adjacent peaks are determined to be within adjacent sectors. Recalling that one sector is 120 milliseconds wide, peaks in adjacent sectors could not possibly represent the S1, S2 heart sounds. Thus if any of the two peaks are in adjacent sectors, a control is passed to command box 828 where the smaller of the two peaks is disregarded and control is passed back to command box 826 to store the next largest of the three peaks. This culling process is performed until the two largest peaks in non-adjacent sectors is found. Control is then passed to command box 829 to calculate time interval between the two largest peaks. Time interval between these two peaks determine the systolic and diastolic periods since the time from the first to the second peak corresponds to the systolic period and the second peak to the third peak the diastolic period (remembering that peak 3 and peak 1 correspond to sequential S1 heart sounds).

Once the location and time intervals for the S1, S2 heart sounds is determined, control is passed to decision box 830 which determines whether the time interval of peak 1 and peak 2 (corresponding to the systolic period) is equal to 25-40% of the time interval of peak 1 to peak 3 (the sum of both the systolic and diastolic periods for the entire cardiac period). If the first perceived time interval is not within this range, the order of the comparison is reversed in decision box 831 and a question is asked whether the time interval between peak 2 and peak 3 is equal to 25-40% of the time interval of peak 1 to peak 3. Thus between decision boxes 830 and 831, the software routines are attempting to determine which time interval corresponds to the systolic period and which time interval corresponds to the diastolic period. If the two time intervals cannot be determined, control is passed to command box 835 which causes the LCD display to display the message "no S1/S2 detected" corresponding to an error condition in which the microprocessor cannot determine the type of cardiac waveform being received. In the event of this error condition, control is passed via continuation bubble B to FIG. 4A to begin the entire process of receiving new waveforms and generating a new diagnostic matrix.

If, however, the time intervals are determined to be systolic and diastolic intervals, control is passed to command box 832 or command box 833 depending upon whether the first time interval is determined to be the systolic or diastolic interval.

Whatever the determination, control is then passed to decision box 834 to determine whether the time interval between peak 1 and peak 3 is within the limits of other sternum locations. Thus the auscultation waveforms received at different sternum locations are compared to determine whether the time intervals (taken at different real time intervals) correspond to reasonably similar time intervals. If a time interval did not correspond, then control would be passed to command box 835 where the error condition display would once again be shown. If the time intervals were shown to correspond, control would be passed from decision box 834 to return box 836 where the subroutine would return to its calling location in the main routine.

Figure 8D:
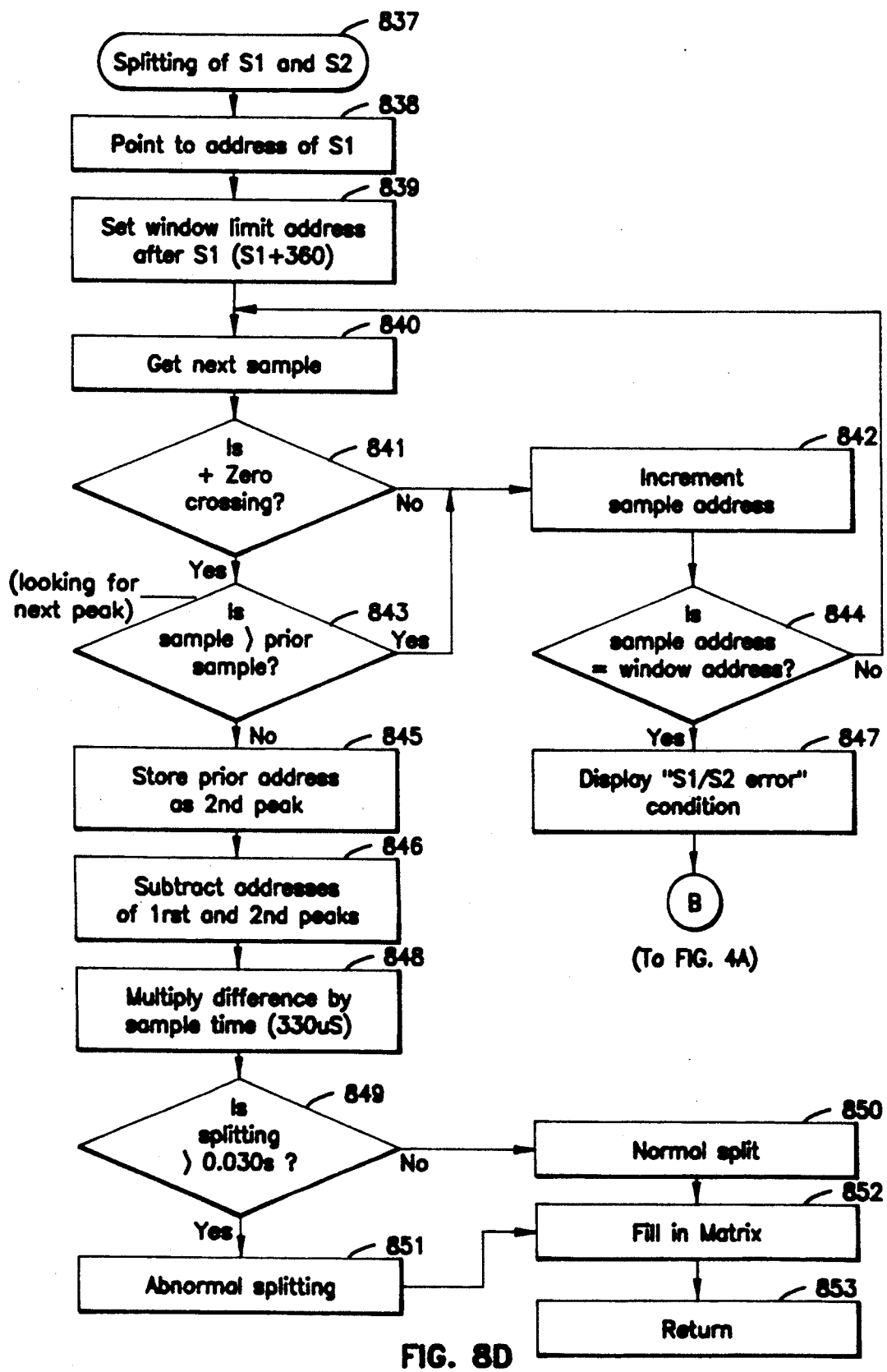

Referring to FIG. 8d, the splitting of S1 and S2 subroutine is described. The main calling routine of FIG. 8a calls the splitting routine and control is entered via command box 837. Command box 838 receives control and the routine sets the address pointer to point to the address of S1 within the stored display of the cardiac waveform for a particular sternum location. A window is set by command box 839 to correspond to the address of S1 plus 360 sample periods. This window is the time limit window established by the program for determining the splitting of the waveform. Any data outside of this time window will be ignored. Control is passed to command box 840 where a major loop is entered to determine the adjacent peak within the window. In order to determine the adjacent peak, each individual data sample must be analyzed since the adjacent peak may be very close in time within the window.

Control is passed to decision box 841 which determines whether the sample under investigation is positive with respect to a zero crossing. If not, the sample addresses is incremented in command box 842 and control is passed to decision box 844 where the sample address is compared against the window address to determine whether the end of the window has been reached. If the end of the window has not been reached, the loop continues back to command box 840 where the next sample or the sample pointer is incremented to continue to search for the adjacent peak. If however the sample address equals the window address at decision box 844, control is passed to command box 847 where an error condition is displayed corresponding to the fact that an adjacent peak could not be found next to the S1 heart sound thus indicating that a S1/S2 split could not be calculated or determined from the stored waveform. In the event of this error condition, control is passed via continuation bubble B to FIG. 4a to reload the diagnostic matrix with new data in an attempt to perform an accurate diagnosis.

If however at decision box 841 it is determined that a zero crossing has been located and the signal excursion is positive, the peak of that signal excursion is searched by decision box 843. Thus in this decision box, the present sample is compared against the prior sample to determine whether the present sample is greater. If the present sample is greater than the prior sample then the peak of the positive going excursion has not yet been determined and the loop is continued to get the next sample within the window in an attempt to find the adjacent peak of the S1/S2 split.

If the present sample is less than the prior sample as determined by decision box 843, the prior sample must have been the adjacent peak for the S1/S2 split. In this event control is passed from decision box 843 to command box 845 to store the prior address as the second peak in the split. Control is then passed to command box 846 in which the addresses of the first and second peaks are subtracted. Control passing through command box 848 finds a multiplication of the difference between the first and second peaks by the sample time (selected in the preferred embodiment of the present invention to be 330 microseconds) to determine the time period between the split. Control passing to decision box 849 calculates whether the split between the S1 and S2 waveforms is greater than 0.03 seconds. If the S1/S2 split is between 0.03 seconds, this is determined to be a normal split and control is passed to decision box 850. This is a commonly found physiologic condition in which an S1/S2 split is a benign condition when it is less than 0.03 seconds.

If, however, the S1/S2 split is greater than 0.03 seconds, an abnormal split is determined and control is passed to command box 851. Command is immediately then passed to command box 852 to fill in the matrix location corresponding to the S1/S2 split. Referring briefly to FIG. 7, the information regarding the S1/S2 split is placed in matrix locations 3 and 4 corresponding to whether the S1 is normally split or the S2 is normally split, respectively.

Figure 8E:
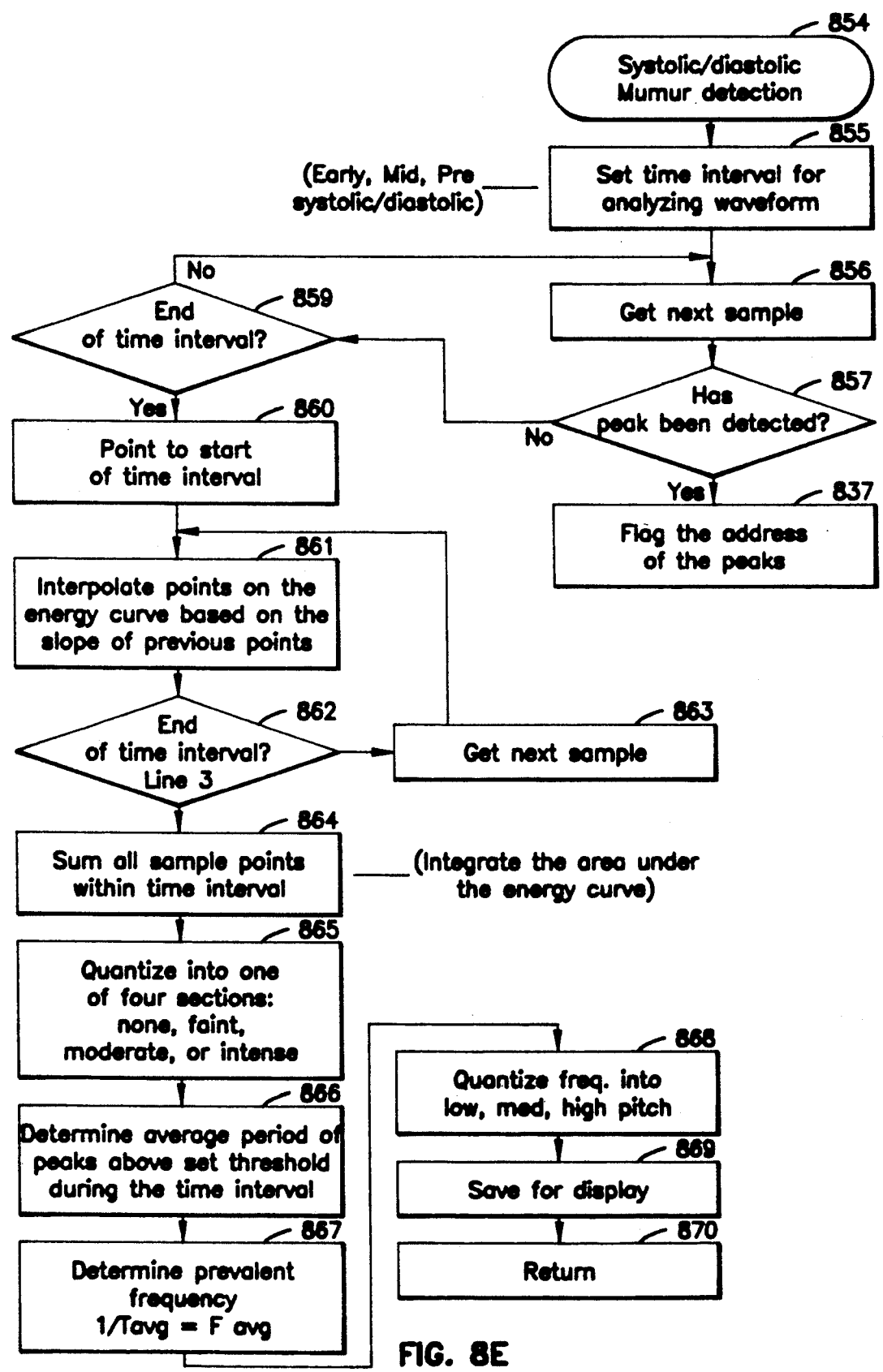

Referring to FIG. 8e, the detailed software flow charts describe the systolic/diastolic murmur detection subroutine. Control is received from the main calling routine of FIG. 8a at location 806. Control is passed to the subroutine via an entry point 854 and a time interval is set for analyzing the waveform at command box 855. The types of time intervals that may be analyzed are within the systolic and diastolic periods, the early, mid and pre intervals. Control passing to command box 856 comprises a minor loop in which the samples of the selected interval are polled to compile a list of all of the peaks within that sample period. Control passing to decision box 857 determines whether a peak has been detected. Peak detection in this instance is similar to the type of peak detection described in the software routines described above. If a peak has been detected, control is passed to command box 858 where the address of the peak is recorded in a list. Control in either case is passed to decision box 859 which calculates whether the end of the selected time interval has been reached. This completes a closed loop for finding all of the peaks within a selected time interval and recording these peaks in a list.

Once the list is completed and the end of the time interval has been found, control is passed to command box 860 where a pointer is set to the start of the interval once again. Control is then passed within a loop starting at command box 861 to interpolate points on a energy curve based on the slope of the peak points recorded in the aforementioned list. The purpose of interpolating points along a curve based on the peaks of the points in the interval is to calculate an energy envelope for the murmur. Control is passed to decision box 863 which queries whether the end of the interval has been reached. If not, control is passed to command box 862 to increment to the next sample of time within the preselected time interval and the energy envelope loop is completed. Once all of the points along the energy curve have been interpolated and an energy envelope has been calculated, command is passed to command box 864 where all of the sample points within the time interval are summed in a conventional fashion well known to those skilled in the art in order to integrate the area under the energy curve to determine the power envelope.

Control has been passed to command box 865 to quantize the energy envelope into one of four discrete descriptions. These descriptions are a short hand or quantized description of the energy envelope and correspond to none, faint, moderate or intense murmurs. Those skilled in the art will readily recognize that the types of data described herein and in particular the types of data for describing the energy envelope of the murmur detected by the present subroutine could be described in greater or lesser granularity by including a quantization of the perceived signals into a greater or lesser number of variables. Those skilled in the art will readily recognize that the matrix corresponding to the perceived signals and the matrices corresponding to specific abnormalities of the body could be of a greater or lesser dimension depending upon the granularity required. In the preferred embodiment of the present invention a specific number of variables corresponding to a granularity required for accurate diagnosis has been selected. Over time however it may be determined that a greater or lesser number of variables within the matrix may be advantageous depending upon the application of the present invention for diagnosing abnormalities in heart, lungs, bruits, etc.

Once the murmur is quantized into one of four sections, control is passed to command box 866 which determines the average number of peaks above a preset threshold during the time interval being analyzed. These number of periods above a threshold is useful for calculating the prevelant frequency of the murmur as calculated in command box 867. This frequency information is used along with the quantized energy of the murmur for answering questions 5 and 6 of the matrix in FIG. 7. In addition to answering these simple questions, this information is stored for later analysis by the detailed diagnostic algorithms which determine the severity of the abnormality and other detailed descriptions regarding the diagnosis. (For example see the detailed description of the diagnostic algorithms for mitral stenosis in FIGS. 8f and 8g requiring a description of the energy envelope of the murmur.)

Once the frequency and quantization has been calculated, the information is saved for the display in command box 869 and control from the subroutine is passed via a return command box 870 to the main calling routine in FIG. 8a.

The main routine of FIG. 8a and the subroutines of FIGS. 8b through 8e describe the detailed software algorithms used for filling the diagnostic matrix and comparing the matrices against stored matrices to determine the type of perceived abnormality of the heart at a certain level of diagnostic detail. The present invention allows for a more detailed analysis of the specific diagnosis of the intelligent stethoscope. This is accomplished by entering one of a plurality of detailed diagnostic algorithms corresponding to any one of the ailments uncovered by the gross algorithm. In the present example, mitral stenosis is a gross diagnosis of a heart ailment which cries for a more detailed diagnosis due to its variant forms. A wide variety of forms and severity of mitral stenosis require a more detailed diagnostic algorithm be used to determine these factors. The present invention includes this type of diagnosis.

Figure 8F:
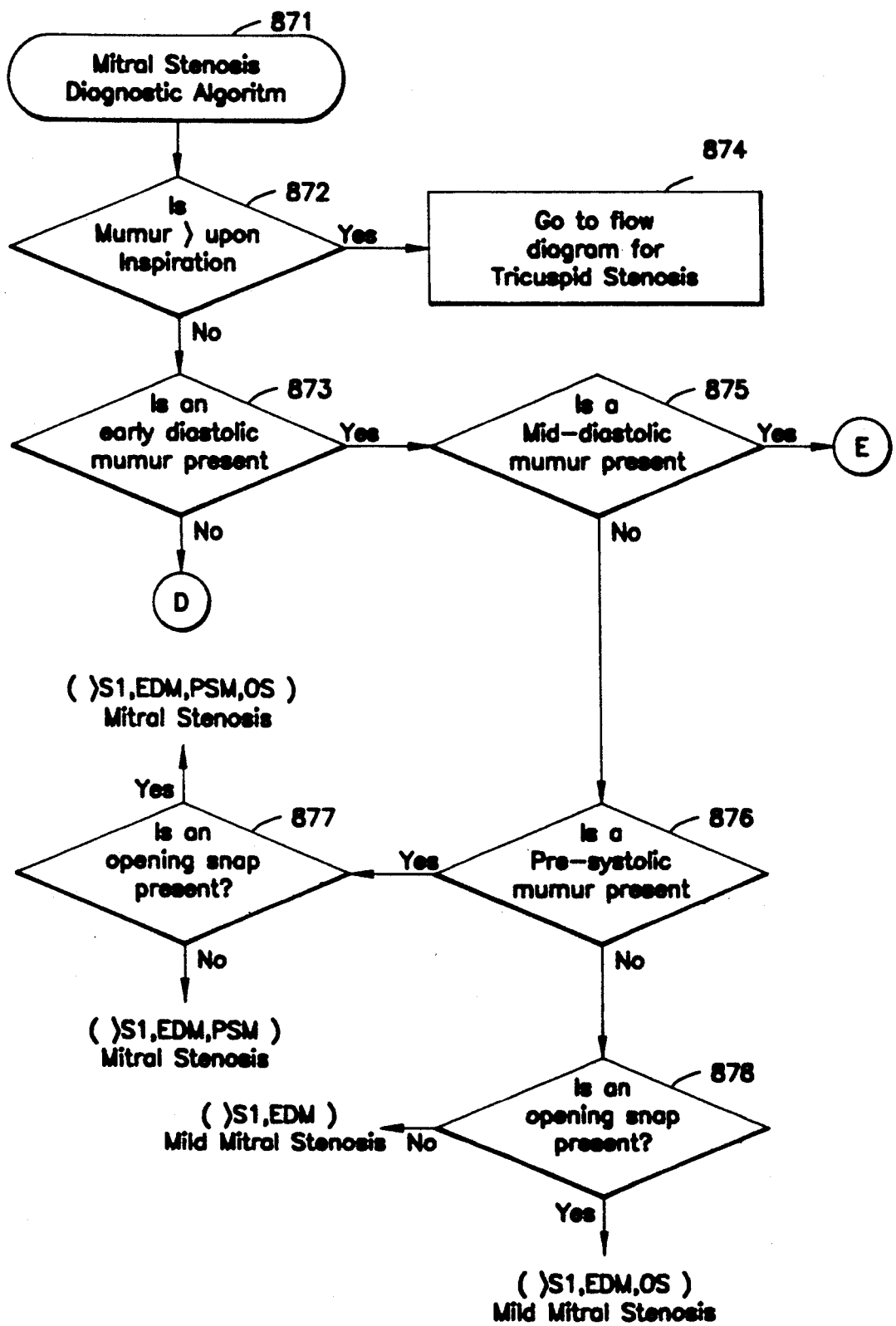
Figure 8G:
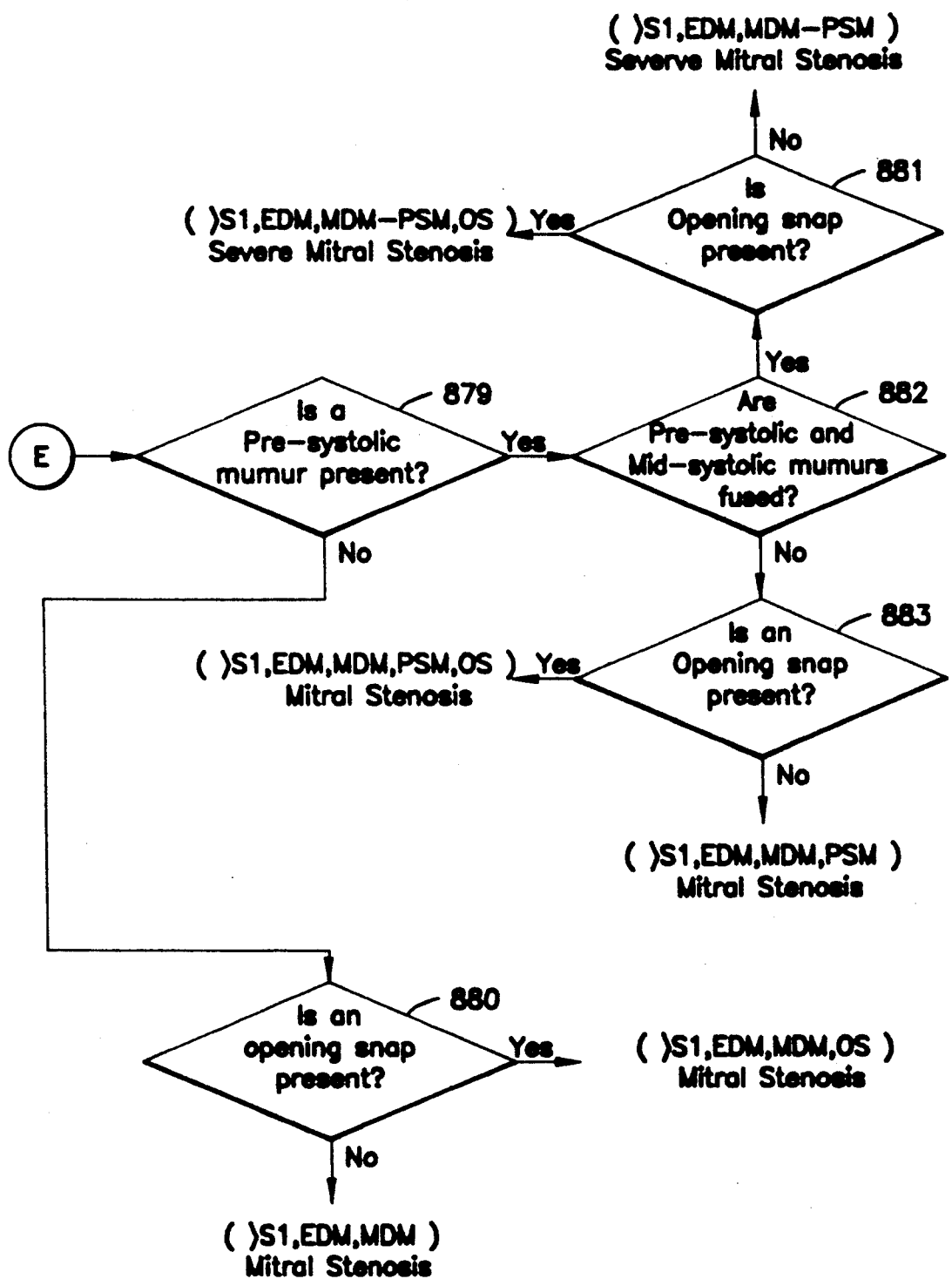
Figure 8H:
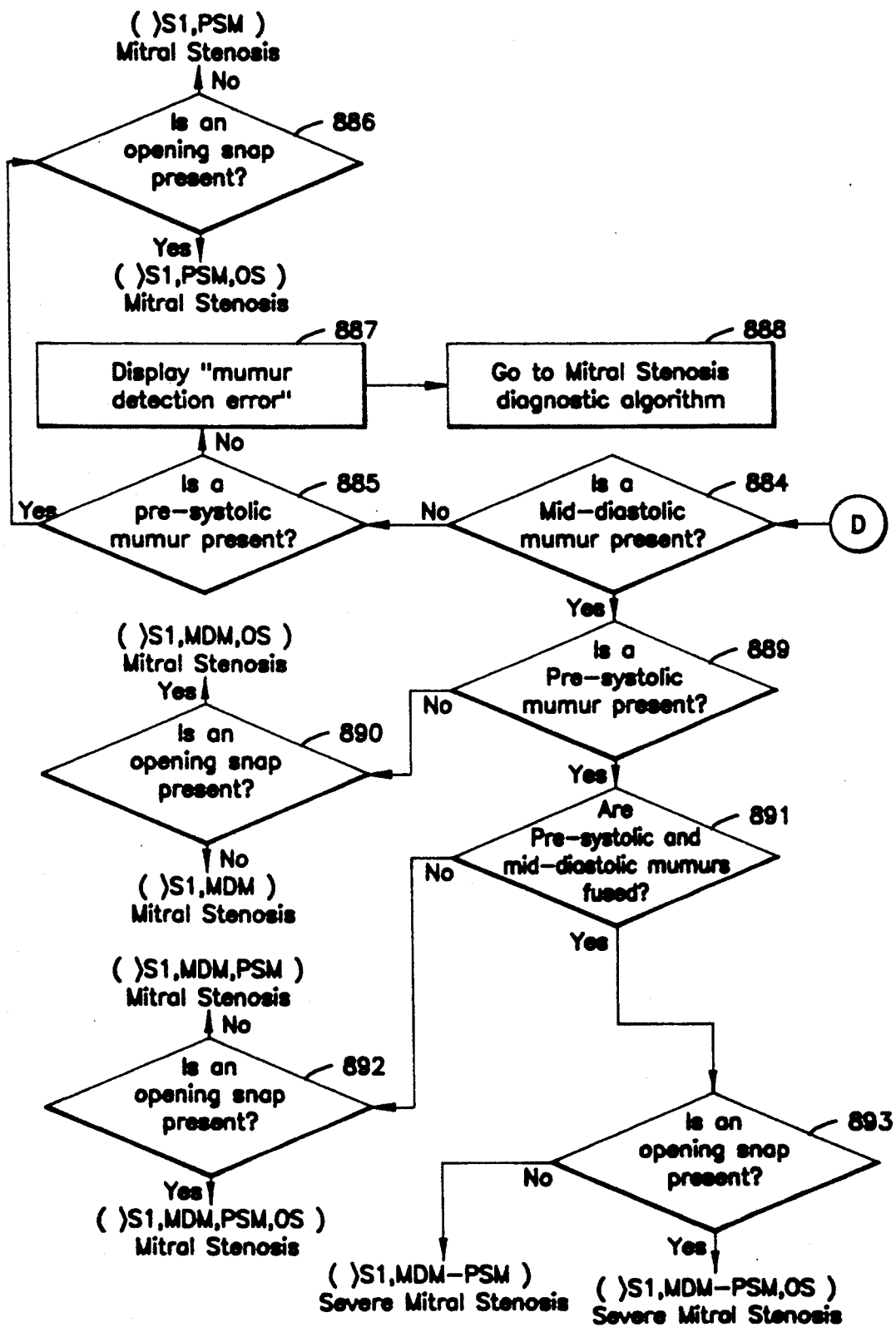

The detailed algorithm for mitral stenosis diagnosis is described is FIG. 8f and 8g. This algorithm is described in a less detailed form than the foregoing algorithms due to the readers heightened understanding of the operation of the present invention based on the foregoing software and hardware descriptions. For purposes of clarity and brevity, many of the mundane details of software operation have been eliminated in favor of an accelerated description of the operation of the diagnostic algorithms.

Once mitral stenosis was diagnosed in the main calling routine, the mitral stenosis diagnostic algorithm is entered via entry point 871. Decision box 872 determines whether the murmur is greater upon inspiration. This calculation is prompted by the display asking the physician to take cardiac samples upon inspiration of the patient. If the murmur is found to be greater upon inspiration, control is passed to command box 874 which determines that tricuspid stenosis is the correct diagnostic procedure which invokes an entirely new algorithm for the detailed diagnosis of tricuspid stenosis. If however the murmur is unchanged upon inspiration, control is passed to decision box 873 in which an early diastolic murmur is reviewed. To determine whether an early diastolic murmur is present, this decision box implies the use of the systolic/diastolic murmur detection subroutine, described above, to aid in making this decision. If an early diastolic murmur is found to be present control is passed to decision box 875 in which once again the systolic/diastolic murmur detection subroutine is invoked to determine whether a mid-diastolic murmur is present. In a like fashion, decision boxes 876 and 879 question whether presystolic murmurs are present in addition to the mid-diastolic murmur. Thus in the same fashion, the systolic/diastolic murmur detection subroutine is used to answer these questions.

The complete understanding of the mitral stenosis diagnostic algorithm contained in 8f and 8g is readily apparent upon following the flow diagrams described therein. The combination of the various attributes of a mitral stenosis condition as evidenced by the auscultation data stored by the present invention will indicate the severity and type of mitral stenosis diagnosed. It is therefore left to the reader to review the mitral stenosis software flow chart for determining the severity and type of mitral stenosis as described in FIGS. 8f and 8g.

Other Heart Sounds Identified

Other types of heart sounds and their associated detailed diagnostic algorithms will be readily apparent to those skilled in the art upon reading and understanding the present specification and drawings. The present invention is readily applicable to the diagnosis and analysis of a wide variety of other heart sounds as well as other body sounds as described below. While the applicant has not described the matrices required for the diagnosis of all of the heart abnormalities described herein, those skilled in the art will readily recognize from the medical descriptions described herein and those found in generally available medical literature, the matrices needed to be stored within the software of the present invention in order to diagnose these abnormalities.

The following description of other heart sounds do not necessarily include the matrices required for their diagnosis for brevity and clarity. Those skilled in the art can construct the necessary matrices from a simple reading and understanding of the present patent application. Those skilled in the medical arts will also recognize a wide variety for abnormalities not described within this patent application which may be used with the present invention for diagnosing other ailments.

1. NORMAL HEART SOUNDS

The normal audible sounds from the heart are made up of the first heart sound produced by the closure of the tricuspid and mitral valves and the second heart sound produced by the closure of the pulmonic and aortic valves. During systole and diastole there are normally no audible tones although there may be innocent flow sounds detected which are discussed under innocent systolic murmurs. The second heart sound is normally louder and higher pitched than the first heart sound at the apex. There are normally no third or fourth heart sounds, rubs or gallops. The rate and rhythm of the sounds are usually regular. The second heart sound is normally split into two distinct sounds made up of the pulmonic and aortic components, which occurs during inspiration and is best heard at the second or third left intercostal space. The normal duration of the split is 0.3 to 0.4 seconds.

2. VARIOUS ABNORMAL AND EXTRA HEART SOUNDS

A fourth heart sound or atrial sound is due to atrial contraction and may be audible immediately before the first heart sound. It may be produced by either left or right atrial contraction. A left-sided fourth sound is usually best heard at the apex and is loudest on expiration. A right sided fourth heart sound is best heard along the left border of the sternum and is increased by inspiration.

The fourth heart sound is low pitched in the 40 to 60 cps range though may be higher pitched. The interval between the fourth heart sound and the first heart sound usually varies with the severity of the condition producing the fourth heart sound: as the condition improves the interval between the two sounds shortens.

The presence of a fourth heart sound may be a normal finding in some individuals but often signifies a disease state, such as systemic hypertension, an ischemic episode of the heart following acute myocardial infarction, myocardiopathies, ventricular hypertrophy, fibrosis, delayed atrialventricular condition or other myocardial diseases.

Ejection sounds or clicks occur in early systole and are often associated with pathologic states such as the presence of a stenotic, but mobile, semilunar valve, the ejection of a greater than usual amount of blood by the left or right ventricle or both, by a more forceful ventricular ejection due to the presence of hypertension in the aorta or pulmonary artery, or the presence of marked dilatation of the pulmonary artery or aorta. Ejection sounds may be produced on the right side (pulmonary ejection sounds) or on the left side (aortic ejection sounds) of the heart.

The pulmonary ejection sounds are usually of maximum intensity in the second or third left interspace or along the left sternal border. They are sharp and clicking in quality and louder in expiration and fainter or actually disappearing in inspiration. They occur in most cases of pulmonary valve stenosis, primary and secondary pulmonary hypertension and conditions associated with increased right ventricular output such as atrial or ventricular septal defect.

The aortic ejection sounds are usually of maximum intensity at the apex and are not affected by respiration. They are almost always present in cases of congenital aortic stenosis and tend to be click-like in quality and occasionally present in rheumatic aortic stenosis and systemic hypertension. They are commonly present in cases of aortic regurgitation, and only on rare occasions in normal individuals with an overactive heart.

Systolic clicks are sharp clicking sounds which generally occur later in systole than ejection sounds, although they may occur during any part of systole. They are usually single but may be multiple and are usually best heard between the left lower sternal border and the apex. These sounds have been heard in connection with pericarditis, mitral valve prolapse with or without mitral regurgitation and in the click-murmur syndrome associated with idiopathic mitral prolapse. Both atrial and ventricular dysrhythmias occur in the click murmur syndrome and sudden death is a reported complication.

Third heart sounds may be normal or abnormal depending on the age and clinical condition they occur in. They occur rather frequently in children and young adults but infrequently in persons over the age of thirty with normal hearts. It is usually best heard at the apex from the left side of the heart, but may be also heard from the right side of the heart in pathological conditions changing the PMI to the lower left sternal border, or around the xiphoid in emphysematous people. Left sided third heart sounds tend to be louder during expiration as opposed to right sided heart sounds that tend to be louder during inspiration.

Third heart sounds occur 0.13 to 0.18 seconds after the second heart sound, making its timing later than that of an opening snap of the mitral valve or the second component of a split second sound, and are lower in pitch. They occur early in diastole during normal heart rates, but as the rates increase they maintain their relation to the second sound and may become mid-diastolic or presystolic. When third heart sounds are loud and benign they tend to disappear when the person sits up or stands up, but when associated with pathology they tend to persist although diminish in intensity A pathological condition associated with a left third heart sound is left sided ventricular failure from any cause. Pathological conditions associated with right third heart sounds are pulmonary hypertension, pulmonary embolus, some congenital heart diseases, and right ventricular failure. Third heart sounds also occur in myocardiopathies. A right and left third heart sound may occur in right and left ventricular failures.

Pericardial knocks are of higher frequency and heard closer to the second heart sounds than the third sounds and occur in early diastole. They are associated with constrictive pericarditis.

Summation sounds are caused by the merging of third and fourth heart sounds and occur most commonly in ventricular failure from coronary artery disease, hypertension, acute myocardial infarction and myocardiopathies.

3. MITRAL REGURGITATION

This murmur has its PMI at the apex and is usually holosystolic, especially if moderate to marked in intensity. It is poorly transmitted above the 3rd intercostal space into the basal area, unless the murmur is very loud (as in the case of ruptured chordae tendineae). The matrix for diagnosing this abnormality is found in FIG. 9C.

When the murmur is faint it is high pitched and blowing, and as it gets louder it becomes harsher. The murmur either does not change or diminishes in intensity with inspiration. In severe mitral regurgitation the second heart sound may be abnormally split and the pulmonic component of the second heard sound may be increased in intensity. A third heart sound may be present in severe mitral regurgitation. There is good correlation with the intensity of the murmur and the degree of mitral regurgitation. If no systolic murmur is heard in the second right intercostal space, a high pitched systolic murmur of maximum intensity at the apex is almost surely due to mitral regurgitation.

4. MITRAL VALVE PROLAPSE

This murmur has its PMI at the apex, begins about one third or halfway into systole and is due to mitral insufficiency. Mid-systolic clicks mark the onset of the systolic murmur.

Late systolic murmurs secondary to mitral valve prolapse can have a loud musical character. If the chordae tendineae rupture this murmur becomes holosystolic. An early diastolic murmur of high frequency, heart best at the apex, can also be an associated finding. A characteristic auscultatory finding is that the mitral click often moves toward the first heart sound or merges with it as the person stands upright, and may become louder and of longer duration. Conversely, prompt squatting causes the click and murmur to move later into systole.

5. TRICUSPID STENOSIS

This murmur has its PMI at the left lower sternal border, is diastolic, and has similar timing, pitch and quality characteristics as mitral stenosis, but is higher pitched and earlier in diastole. The first heart sound is less commonly accentuated as in mitral stenosis. Tricuspid stenosis practically always occurs in association with other mitral lesions such as mitral stenosis. The diagnosis really depends on the location of the PMI and its reaction to respiration. It usually is well localized at the lower left sternal border and does not extend far to the left on the chest wall. It increases in loudness with inspiration usually several-fold, whereas mitral stenosis is either unchanged or decreased. The matrix for diagnosing this abnormality using the present invention is shown in FIG. 9d.

6. TRICUSPID REGURGITATION

This murmur has its PMI at the left lower sternal border and when loud tends to be holosystolic. The PMI can vary from the left lower sternal border to the midclavicular line depending on the ventricular size. It is high pitched and blowing and can be harsh when loud. The murmur increases in loudness with deep inspiration and usually normal inspiration, but this may not occur with severe regurgitation. In severe regurgitation a third heart sound and a mid-diastolic murmur often occurs.

7. VARIOUS TYPES OF AORTIC STENOSIS, EXAMPLES OF WHICH ARE SUPRAVALVULAR, VALVULAR AND DISCRETE SUBVALVULAR AORTIC STENOSIS

The systolic murmur in all three types of aortic stenosis is harsh, diamond shaped and ends before the aortic second sound. The matrix for diagnosing this abnormality using the present invention is shown in FIG. 9a.

Valvular aortic stenosis has its PMI at the first or second right intercostal space and is systolic. When moderate to severe it tends to be crescendo-decrescendo, peaks in mid-systole, is diamond shaped and stops before the second heard sound. When mild the murmur may be shorter and reach a peak in early systole. Faint murmurs tend to be rough and medium pitched while louder murmurs are harsh. Moderate murmurs are well transmitted to the apex and neck. In emphysematous patients, the murmur is often louder at the apex than the second right intercostal space. In severe stenosis the second heart sound may be absent in the second right intercostal space but may be still present at the apex.

In subvalvular stenosis the PMI is generally lower in the third left intercostal space. A very valuable auscultatory finding may be an aortic ejection sound which almost always occurs in congenital valvular stenosis, infrequently in subvalvular stenosis and rarely, if at all, in supravalvular stenosis. Aortic regurgitation may occur in all three types. The intensity of the aortic closure sound may be normal, increased, or decreased in all three, but is commonly normal or increased in valvular stenosis unless the valve is calcified, in which case it is decreased. It is usually decreased in subvalvular stenosis. Splitting of the second heart sound may be normal in all three, or the sound may be single. If the stenosis is severe, a paradoxical splitting will occur.

A fourth heart sound will occur in any of the stenoses and is an indication of the severity of the stenoses since it occurs with the more significant grades of stenoses, and a third heart sound signifies even more significant stenosis.

The presence or absence of a systolic ejection sound may be the most valuable single auscultatory sign in separating valvular from other types of aortic stenosis. However, a loud murmur may mask the ejection sound making it difficult to hear by the human ear. This instrument will not have this masking difficulty.

8. AORTIC REGURGITATION

This murmur has its PMI at the right or left third intercostal space, is diastolic, high pitched, soft, blowing and decrescendo. It usually occurs in early diastole but may last throughout diastole. It begins with the aortic component of the second heart sound. When an S3 gallop is present it indicates left ventricular dysfunction. In acute severe regurgitation the murmur is short, soft medium pitched and impure. In chronic severe regurgitation the murmur is long, blowing, high pitched and pure. The murmur can be crescendo early and then become decrescendo. The aortic component of the second heart sound is increased. The matrix for diagnosing this abnormality using the present invention is shown in FIG. 9b.

9. ATRIAL SEPTAL DEFECT

This murmur has its PMI at the second or third left intercostal space, is systolic with a widely split second heart sound. The second heart sound is almost always split in inspiration and expiration at the apex and left sternal border. The splitting is usually fixed but may vary with respiration. The murmur is not as harsh as in ventricular septal defect. A rumbling mid-diastolic murmur may occur. When pulmonary hypertension occurs in conjunction with atrial septal defect a right sided fourth heart sound may occur, along with an increased second heard sound. Along with pulmonary hypertension the pulmonary flow murmur decreases, the mid-diastolic murmur decreases or ceases, a pulmonary ejections sound develops, an early diastolic murmur of pulmonary regurgitation frequently develops, splitting of the second heart sound decreases but is rarely normal and a systolic murmur of tricuspid regurgitation develops with right sided ventricular failure.

In differentiating the mid-diastolic murmur of atrial septal defect from mitral stenosis, if the murmur is loudest over the right ventricle and increases with inspiration it is due to atrial septal defect. If it is loudest over the left ventricle and decreases or does not change with inspiration it is due to mitral stenosis.

10. VENTRICULAR SEPTAL DEFECT

This murmur has its PMI at the left third or fourth intercostal space, is poorly transmitted to the neck, is holosystolic and diamond shaped but can end before the second heart sound with small defects. The murmur tends to be high pitched and louder murmurs are harsh. A third heart sound can occur at the apex. A rumbling apical systolic murmur may be present. When this murmur occurs along with pulmonary hypertension, i.e., Eisenmengers complex, it is less intense and less harsh with large shunts or even ceases to be holosystolic, the pulmonic component of the second heart sound is increased and the splitting of the second heart sound is decreased, a pulmonary ejection sound can be heard.

In very high septal defects a systolic murmur along with an early diastolic murmur can be "to and fro" as in patent ductus arteriosus but the PMI is lower. An apical diastolic flow murmur can also be present.

11. PATENT DUCTUS ARTERIOSUS

This murmur has its PMI at the second left intercostal space at the left sternal border and is "machinery" in quality. It is a continuous murmur in systole and diastole and usually masks the second heart sound. It starts with the first heart sound, increases in intensity to the second heart sound and then decreases, reaching a minimum at the time of the next first heart sound. Not all of these murmurs are continuous though and they may start after the first heart sound and fade before the next first heart sound. When this murmur is associated with a large shunt paradoxical splitting of the second heart sound may occur, but the first heart sound is usually unchanged. A third heart sound may occur in children. A diastolic rumble may occur. In the presence of pulmonary hypertension, the diastolic murmur disappears first, then the systolic component.

12. TETRALOGY OF FALLOT

This murmur has its PMI at the third or fourth left intercostal space, is systolic, harsh, and fades or stops before the second heart sound. The second heart sound is usually not abnormally split, but is heard to the left of the sternum due to the displacement of the aorta in this condition. There is generally an inverse relationship of the loudness of the murmur with the degree of the condition.

13. INNOCENT SYSTOLIC MURMURS

There are generally two types of innocent systolic murmurs, the apicosternal with its PMI generally at the apex and the other with its PMI at the second left intercostal space. The apicosternal type is the most common murmur in children, is well transmitted to the neck, apex and aortic area, and is almost always heard in the pulmonic area no matter where the PMI is located, which is a distinguishing characteristic. The murmur occurs in early or mid-systole, but late systole is quiet. It is usually crescendo-decrescendo, medium pitched and rough, but not harsh. It is usually not high pitched. It often has a vibratory quality and quite loud in children. It is usually louder at the left sternal border than at the apex. Held expiration usually increases the intensity of the murmur. The first and second heart sound are normal.

The other type has its PMI well localized at the second left intercostal space and is not widely transmitted over the precordium. It is rough, increased in intensity in held expiration, and the first and second heart sounds are normal.

14. PULMONARY HYPERTENSION

This condition is noted by an accentuated second heart sound, a pulmonary ejection sound, a frequent early diastolic murmur of pulmonary regurgitation along with right ventricular failure, a frequent loud systolic murmur of tricuspid regurgitation if pulmonary hypertension is severe and a decreased splitting of the second heart sound. It is rare for the splitting of the second heart sound to be normal or absent.

15. SYSTEMIC HYPERTENSION AND ARTERIOSCLEROSIS

This is a common murmur in the elderly, is systolic and usually located at the base rather than the apex, and medium pitched. It is not as loud as the murmur of aortic stenosis and it is well transmitted to the apex. The aortic component of the second heart sound is normal or accentuated in patients with hypertension or arteriosclerosis but is often diminished or absent in organic aortic stenosis Abdominal murmurs due to luminal narrowing of the aorta may be heard in advanced arteriosclerosis.

16. COARCTATION OF THE AORTA

This murmur has its PMI usually in the second left intercostal space, occasionally on the right and rarely at the apex. It usually causes a basal systolic murmur and not infrequently is diastolic as well. One important feature of this murmur is that it is often louder in the posterior interscapular region than it is anteriorly. A biscuid aortic valve occurs very frequently in patients with coarctation. Varying degrees of aortic stenosis, regurgitation or both may be present. An ejection sound is usually heard at the apex. An accentuated aortic second sound may be present. A systolic continuous murmur or hum may be present with an associated thrill and palpable systolic pulsation at the sternal notch. Of further diagnostic value is the presence of elevated blood pressure in the upper extremities compared to the lower extremities and a lag between the brachial and femoral pulses.

17. PULMONARY REGURGITATION

This murmur has its point of maximum intensity in the second or third left intercostal space, is high pitched, is almost always associated with pulmonary hypertension and an accentuated second heart sound, and a pulmonary ejection sound may be present. It has the same timing, pitch and quality as the murmur of aortic regurgitation. Following surgery for pulmonary stenosis, marked pulmonary regurgitation may occur. This murmur is often short, rough, diamond shaped and a short interval may be present between the second heart sound and the onset of the murmur.

In differentiating this murmur from others (i.e. aortic regurgitation) it is important to note that the murmur usually has a loud pulmonic second sound, no evidence of rheumatic heart disease, no peripheral evidence of aortic regurgitation, no murmur present in the second right intercostal space and is louder on inspiration than on expiration.

18. PERICARDIAL FRICTION RUB

This sound is produced by the parietal and visceral surfaces of roughened pericardium rubbing on each other, is usually heard between the apex and the left lower sternal border but may be widespread. It may consist of a presystolic component due to atrial contraction, a systolic component due to ventricular contraction and a diastolic component due to rapid filling of the ventricle. The sound has a quality described as scratching, grating or rasping and at times may be musical. It occurs in myocardial infarction, idiopathic pericarditis, rheumatic pericarditis and in postoperative people who have had heart surgery where it is usually loudest in the left third or fourth intercostal space. A characteristic feature is its variability with body positioning and its accentuation with held inspiration.

Free air in the mediastinum may be confused with a pericardial friction rub but is high pitched and crackling, confined to systole and has a "crunching quality" (Hamman's sign). Some of the conditions producing this entity include thoracotomy and esophageal rupture.

19. CARDIAC ARRHYTHMIAS

Any definitive diagnosis of a rhythm disturbance of the heart requires an electrocardiogram, although auscultation frequently yields diagnostic clues to cardiac arrhythmias.

Heart rates of less than fifty beats per minute are defined as bradycardia and rates above one hundred are defined as tachycardia. The rhythm may be regular or irregular as noted by the interval timings between cardiac cycles or the intervals between the first heart sounds.

Sinus tachycardia generally has a cardiac rate of 100–180, regular rhythm, the first heart sound has a constant intensity and the first and second heart sounds are normally split. Paroxysmal atrial tachycardia has similar findings as sinus tachycardia with the exception of a faster rate of 140–200.

Atrial flutter (usually 2:1 block) generally has a rate of 120–180, regular or irregular rhythm, the first heart sound has a constant intensity and the first and second heart sounds are normally split. Atrial fibrillation generally has a rate of 100–200, totally irregular rhythm, variable intensity of the first heart sound and normal splitting of the first and second heart sounds.

Ventricular tachycardia generally has a rate of 120–200, regular or slightly irregular rhythm, variable intensity of the first heart sound and abnormal splitting of the first and/or second heart sounds. Complete heart block generally has a rate of less than 50, regular rhythm, variable intensity of the first heart sound with a frequently audible atrial sound and normal splitting of the first and second heart sounds.

Ventricular and atrial premature contractions can often be detected by auscultatory methods. They are usually followed by a pause in the cardiac events and the pause following an atrial premature contraction is usually shorter than after a ventricular premature contraction. The heart sounds are usually abnormally split in ventricular premature contractions and not split in arterial premature contractions. The intensity of the first heart sound is generally more accentuated with atrial premature contractions than with ventricular premature contractions. The second sound is generally diminished in both situations and may be entirely absent.

20. PULMONARY VALVULAR STENOSIS WITH AN INTACT VENTRICULAR SEPTUM

This murmur has its PMI in the second left intercostal space, is a harsh systolic murmur, and has the same pitch and quality as that of aortic stenosis and is also diamond shaped. It is associated with a pulmonary ejection sound and often a right sided fourth sound. The murmur usually ends before the pulmonic second sound but may extend through the aortic second sound. The longer the duration and delay of the peak of the murmur the more severe the stenosis. The second heart sound is abnormally split and the degree of splitting and the intensity of the pulmonic second sound are well related to the degree of stenosis.

In isolated infundibular stenosis, the PMI is lower (third or fourth left intercostal space) and there is no ejection sound.

21. POSTSURGICAL SOUNDS

Prosthetic heart valves generally come in four types: Ball in cage, tilting disc, bioprosthesis and the bileaflet type. They may fail for a variety of reasons and have normal and abnormal auscultatory characteristics.

Aortic Prosthetic sounds and murmurs:

The ball in cage type has a characteristic aortic opening and closing click. These sounds are high pitched, loud and distinct. The aortic opening click follows the first heart sound by 0.07 seconds. It is heard best at the apex or lower left sternal border. A harsh, short systolic murmur usually follows and multiple systolic clicks may be heard. The aortic closure click is less prominent than the opening click and occupies the position of the normal aortic component of the second heart sound. Inspiratory widening of the second heart sound usually occurs and there is a diastolic murmur present with a normally functioning valve. Reduction of the amplitude of the aortic opening click is abnormal. If the opening click is of less amplitude than the closing click, thrombosis of the valve or ball variance should be suspected. These complications usually mean aortic insufficiency and a diastolic blowing murmur, which is always an abnormal finding. Absence of the opening click is diagnostic of severe ball variance or thrombosis with marked restrition of ball motion. Beat to beat variation between the first heart sound and the aortic opening click or intermittent absence of the opening or closing clicks is very suggestive of a sticking poppet.

With the bioprosthesis aortic type there is a faint opening sound of the porcine valve following the first heart sound by 0.03 to 0.08 seconds. An early mid systolic, high pitched murmur is heard at the lower left sternal border. Aortic closure is high pitched and discrete in most people and best heard at the second right or left intercostal spaces. It occupies the position of the aortic component of the second heart sound. Diastolic murmurs or sounds are not normally present. A loud ejection murmur occupying most or all of systole suggests fibrosis and calcification of the valve leaflets with resultant stenosis of the prosthesis and a decreased aortic closure sound further supports this. Any diastolic blowing murmur implies malfunction with aortic regurgitation. Early after implantation (one to two years) the dominant frequency of the aortic closure sound is similar to that of a normal aortic valve at approximately 50 Hz. In time, with progressive stiffening of the leaflet, a gradual increase in frequency is observed. Five to eight years after the implantation the frequency may be almost doubled at approximately 80 to 85 Hz, which is similar to a normal aortic valve with stenosis. These changes cannot be appreciated by the human ear, but can be accurately detected with the use of this instrument.

The tilting disc type valve has a faint opening sound that is generally not audible to the human ear but can be detected by this instrument. It follows the first heart sound by 0.03 to 0.08 seconds and an early to mid systolic ejection murmur is commonly present, heard best in the aortic area. The closing sound is distinct, clicky, and of high frequency. Rarely a faint diastolic murmur is heard in a normally functioning valve, indicating slight aortic regurgitation. Decrease or disappearance of the aortic closure sound is abnormal and indicates abnormal motion of the disc. This is usually secondary to thrombosis and is accompanied by significant aortic insufficiency. A diastolic murmur is indicative of disc valve malfunction and secondary aortic insufficiency; however, severe insufficiency could be silent.

The bileaflet type valve has an opening sound that occurs 0.06 to 0.08 seconds after the first heart sound which again may not be audible to the human ear but detectable by this instrument. A soft mid systolic murmur occurs in one third to one half of people and does not in itself mean valve dysfunction. A loud, high pitched, clicky sound occurs in end systole signifying the aortic closure and occupies the aortic component of the second heart sound. It is approximately five times louder than the opening sound. No diastolic sounds or murmurs are heard in patients with normally functioning valves.

Mitral prosthetic sounds and murmurs:

With the ball in cage type the interval between the aortic component of the second heart sound and the opening sound of the valve is usually 0.06 to 0.15 seconds. The mitral opening sound is greater than the closing sound and there is a systolic ejection murmur heard. There is normally no diastolic murmur and a third heart sound is frequently present. A malfunctioning valve is associated with an interval between the aortic second heart sound and the opening of the valve of less than 0.06 seconds or greater than 0.15 seconds. The presence of a diastolic murmur or the absence of an opening sound are also signs of a malfunctioning valve.

With the bioprosthesis type the same interval is 0.07 to 0.11 seconds, has a systolic ejection murmur and a possible diastolic murmur. Abnormalities are associated with a loud diastolic murmur and sometimes a musical murmur of mitral regurgitation.

With the tilting disc type the same interval is 0.05 to 0.09 seconds, a mitral opening sound is very faint and the closing sound is usually easily heard. There is normally a systolic ejection murmur. Abnormalities are associated with a holosystolic murmur of mitral regurgitation, a diastolic murmur, and an absent mitral closing sound in conjunction with a loud systolic murmur which could signify jamming of the disc or acute mitral regurgitation.

With the bileaflet type the same interval is 0.04 to 0.08 seconds and the mitral opening sound is approximately one tenth the amplitude of the mitral closure sound. No murmurs are generally heard in normally functioning valves.

22. ACUTE RHEUMATIC CARDITIS

In this condition the first heart sound may be diminished because of prolongation of atrioventricular conduction. A pericardial rub may be present early. A systolic murmur with the characteristics of an innocent murmur is often heard. A faint murmur of mitral regurgitation may be present early and remain faint or increase rapidly in loudness. An accentuated third heart sound may develop, especially if a loud systolic murmur is present. A mid-diastolic murmur that does not indicate organic mitral stenosis is common. A faint murmur of aortic regurgitation is occasionally present early, often with no other murmur. A pulmonary systolic murmur, musical in quality and varying from day to day occasionally occurs. Less than fifty percent of people who develop acute rheumatic carditis will go on to develop rheumatic valvulitis.

23. ACUTE MYOCARDIAL ISCHEMIA AND INFARCTION

By far the most common of all auscultatory abnormalities present in acute ischemia is a fourth heart sound. During an episode of ischemia, the sound may appear or become prominent. It may become clearly audible with little change throughout the respiratory cycle, whereas in the absence of an ischemic episode it tends to be maximal in expiration. Its intensity with relation to the first sound may increase, and the interval between the fourth and first heart sounds may lengthen. When the ischemic episode has usubsided the fourth heart sound may recede. The fourth heart sound is often inaudible to the human ear but can be accurately detected by this instrument.

In acute ischemia the first heart sound is reduced in intensity and frequency, but may be normal or increased in the company of mitral systolic murmurs. A transient apical systolic murmur of variable quality and duration may occur. On rare occasion the second heart sound may be abnormally split.

In acute myocardial infraction the same findings often occur as described above but may be of longer duration or even permanent. A pericardial friction sound is common and in fact, myocardial infarction is the most common cause of this auscultatory finding. This sound varies with respiration, has a "scratchy" quality, and when fully developed is presystolic, systolic and early diastolic. A loud systolic murmur, high pitched, heard best at the lower left sternal border, with a palpable thrill often signifies perforation of the interventricular septum. A loud systolic murmur which is widely transmitted, heard best at the apex, without a palpable thrill is often a ruptured papillary muscle.

In the chronic stage of myocardial infarction a fourth heart sound is characteristic with occasional apical systolic murmurs and sometimes a third heart sound.

24. AUSCULTATORY SOUNDS IN VARIOUS CONDITIONS:

Endocarditis usually presents with evidence of valvular involvement, and especially the development of a new murmur. If cardiac failure develops, as it usually does, its characteristic features are superimposed upon both the infectious process and any underlying pathology.

Myocardial failure has auscultatory characteristics consisting of a diminished first heart sound, a fourth and sometimes third heart sound, an accentuated pulmonic component of the second heart sound, occasional paradoxical splitting of the second heart sound, occasional occurrence of a systolic murmur of tricuspid regurgitation, rarely an early diastolic murmur of pulmonic regurgitation and in some people an apical middiastolic murmur may be heard.

Cardiac tumors are uncommon, but one type, the intracardiac myxoma, produces characteristic auscultatory findings. A left lateral myxoma produces a middiastolic and presystolic murmur similar to mitral stenosis, although the first heart sound is not accentuated. A variation in the intensity of the murmur in different body positions is diagnostic. Occasionally only a systolic murmur is present due to an extension of the tumor through the mitral valve. An early diastolic sound also occurs. A right atrial myxoma produces a tricuspid systolic murmur more frequently than a diastolic murmur, but either or both may be heard. Unlike left atrial myxomas, right atrial tumors do not usually mimic the auscoltatory findings of tricuspid stenosis. Often, myxomas of either side, but especially of the right atrium, may produce murmurs that are strikingly unlike any murmur one may expect to hear (systolic, diastolic or even continuous), which is another auscultatory characteristic.

Various other uncommon conditions that can present with auscultatory findings including cardiomyopathies, Marfan's disease, pectus excavatum and straight back syndrome, thyrotoxicosis, cardiovascular syphilis, pulmonary embolism, carcinoid syndrome, ankylosing spondylitis with cardiac involvement, rheumatoid arthritis with cardiac involvement and systemic lupus erythematosus. These conditions will also be included in the software analysis.

Lung Mode of Operation

The present invention is applicable to more than simply diagnosing cardiac abnormalities via ausculation. The present invention is also applicable to diagnosing lung abnormalities. As an example of the operation of the present invention for identifying and diagnosing lung abnormalities, the user simply presses the mode key to identify breath sounds (see keyboard 110 identifying the mode key and software locations 412 and 414 of FIG. 4a for identifying the particular mode of operation of the present invention).

Figure 10:
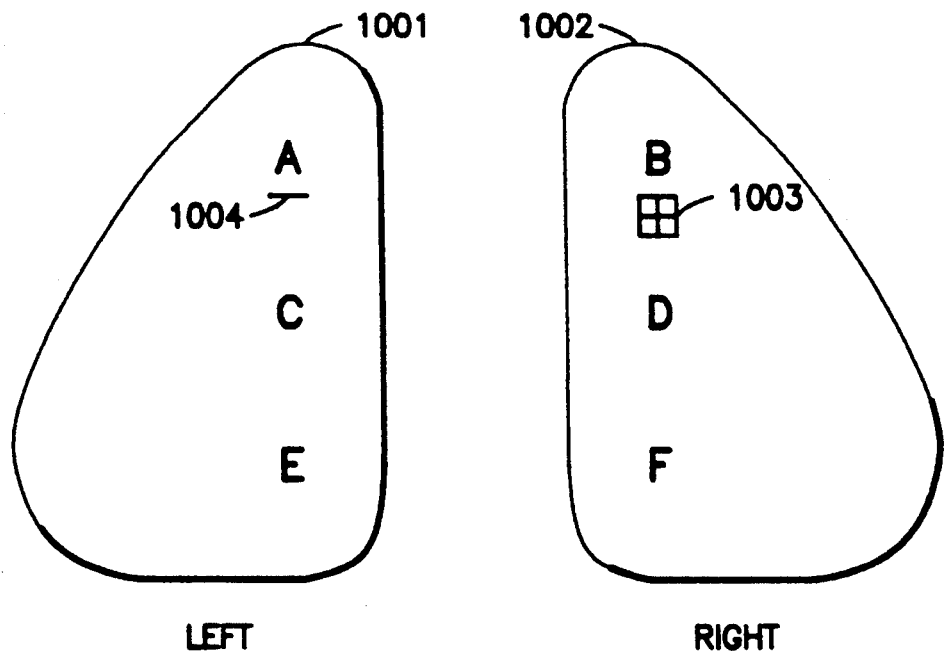
FIG. 10 shows an alternate display for the intelligent stethoscope which directs the specific locations to be monitored for lung sounds for the application of the intelligent stethoscope to lung sounds.

Upon pressing the mode key to change mode of operation of the present invention, the sternum display 601 is replaced by the lung display 1001 and 1002 shown in FIG. 10 and used on the LCD display 102 indicating the breath sounds mode of operation of the present invention. The lung display is similar to the sternum display described above in that the user is prompted as to where to place the bell of the stethoscope to receive auscultation information. For example, in a fashion similar to that used in the sternum display, six locations over the lungs entitled A-F are used to prompt the user as to where to listen and store breath way forms.

Referring to FIG. 10, the lung display is shown. The A means that a waveform taken at location A has been captured and stored in memory. The box display 1003 indicates the next location on the patient that should be probed by the stethoscope bell for storing the lung waveforms into memory.

Normal breath sounds (vesicular breath sounds) are noises with frequencies generally between 200 and 600 Hz, heard through the chest wall of a healthy individual throughout inspiration and at the beginning of expiration. They are generated by turbulent flow in the normal tracheobronchial tree.

Bronchial breathing refers to a higher-pitched and louder sound than normal vesicular breathing. It is normal when heard over the trachea and large bronchi but is abnormal when heard over the peripheral lung.

Crackles (rales) are a sequence of explosive, nonmusical, interrupted (discontinuous) pulmonary sounds with a wide spectrum of frequencies between 200 and 2000 Hz. Wheezes (rhonchi) are musical continuous pulmonary sounds. The musical character of these sounds is the result of harmonically related frequencies which, when recorded, have a regular pattern of identical waveforms.

Adventitious pleural sounds (pleural rub; friction rub) are interrupted, nonmusical sounds similar to the crackles produced by jerky movement of lung over roughened abnormal pleura. Pleural rubs (friction rubs) are usually longer and of lower pitch than crackles arising from the lung. Sometimes they are louder and clicking in nature.

The differential diagnosis of breath sounds depends on frequency, timing, amplitude, transmission and the effect of posture of the sounds obtained. In the lung mode the chestpiece of the instrument is applied to the superior, middle and inferior lung fields from apex to base of each lung, representing a total of six locations (A-F). Areas to avoid are over bone since lung sounds are diminished over these areas. The locations are divided into the three areas of superior, middle and inferior lung fields. Each area is represented by two locations as follows:
1) Superior areas are represented by locations A and B.
2) Middle areas are represented by locations C and D.
3) Inferior areas are represented by locations E and F.

A specific order of auscultation is followed by observing the location of a marker on the LCD lung diagram which constantly illustrates the location to obtain next. (See FIG. 10.) Confirmation that a good signal is obtained in each of the six locations is obtained by visualizing the waveform on the display simultaneously while listening to the audible signal through the earpieces. When the user has confirmed a good signal is obtained, the "capture" button is pushed, which will freeze the waveform on the display. The user can then visually inspect the waveform before sending it to memory by pressing the "enter" button.

The waveform patterns are obtained during the periods of inspiration and expiration in every location. If a poor quality waveform is recorded inadvertently the user is able to record a substitute waveform from a location by moving a cursor to the desired location on the LCD lung diagram and repeating the recording for that location.

At the end of the auscultation sequence all waveform patterns along with their specific locations are used for the software analysis. The software is designed to make six determinations of the waveform pattern obtained at each of the six locations on the chest wall. The six determinations are (see FIG. 11a):
1) Are sounds normal?
2) Are crackles (rales) present?
3) Are wheezes (rhonchi) present?
4) Are adventitious pleural sounds (rubs) present?
5) Are other abnormal sounds present?
6) Intensity comparative analysis The intensity comparative analysis software makes an absolute intensity reading at each location A-F as well as compare the intensity readings of A:B, C:D and E:F. The comparative analysis process is performed by constructing a data matrix incorporating the locations over the lungs with the determinations of the waveform patterns obtained at each location as described in detail above for heart sounds.

Figures 11A, 11B, 12:
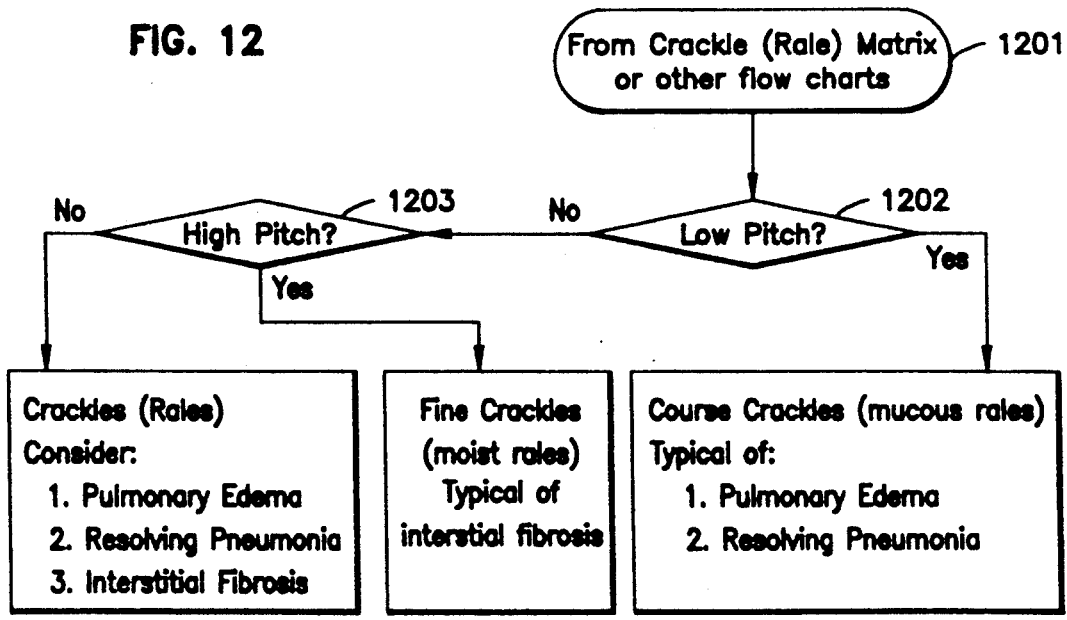
FIGS. 11a and 11b show the lung sounds matrices for a normal lung and for crackles (rales), respectively.
FIG. 12 shows a simplified flow chart for analyzing crackles (rales) from the matrix derived from the lung sounds.

Specific matrices represent normal 1101 or abnormal 1102 waveform patterns as shown in FIGS. 11a and 11b for the normal and crackles (rales) matrices, respectively. Abnormal waveforms determined by individual matrices are further evaluated by specific algorithms similar to the detailed diagnostic algorithm for mitral stenosis described above. The algorithms utilize frequency, timing, amplitude, transmission and effect of posture criteria to yield diagnostic information to the physician. Specific operating instructions are shown on the liquid crystal display at particular algorithm locations when user input is necessary to proceed with an algorithm determination.

The diagnosis matrix for crackles (rales) is shown in FIG. 11b and a simplified software flow chart for this diagnostic analysis is shown in FIG. 12. Once the crackle (rale) diagnosis is determined (at for instance location 811 of FIG. 8a if the mode has been set to lung diagnosis) control would be passed to subroutine entry location 1201 for the crackle (rale) diagnostic routine. Control is then passed to decision box 1202 where the pitch of the crackles is determined. A low pitch may indicate course crackles (mucous rales) typical of pulmonary edema or resolving pneumonia. If, however, a low pitch is not present, control is passed to decision box 1203 where the received data is analyzed to determine whether a high pitch is present. A high pitch indicates fine crackles (moist rales) which are typical of interstitial fibrosis. An indeterminate pitch however would pass control from decision box 1203 onto further routines to consider pulmonary edema, resolving pneumonia, interstitial fibrosis, or other ailments.

Breath Sounds Identified

1. DIMINISHED BREATH SOUNDS

Diminished breath sounds are found in shallow, weak breathing sometimes due to neuromuscular illness. Complete obstruction of a lobar or a segmental bronchus will decrease breath sounds owing to decreased air entry. Destruction of alveolar units, as in emphysema, will result in decreased air entry and decreased breath sounds.

2. ATELECTASIS PNEUMONIA OR FIBROSIS

Airless lung tissue is an excellent conductor of high-pitched prolonged expiratory breath sounds that originate from bronchi adjacent to it. Therefore this high-pitched loud sound may signify that there is atelectasis, pneumonia or fibrosis present.

3. CRACKLES OR RALES

Crackles or rales are short, interrupted, or discontinuous explosive sounds heard through the chest wall late in inspiration when gas suddenly inflates the closed airways or peripheral lung tissue or early in inspiration and expiration when gas is passing through partially obstructed bronchi. Crackles do not occur in healthy lung tissue and their presence indicates an underlying abnormality of the lungs or the pleura. The matrix for diagnosing this abnormality using the present invention is shown in FIG. 11b.

High-pitched crackles that start late in inspiration and become more numerous toward the end of inspiration are typical of diffuse interstitial fibrosis such as fibrosing alveolitis or asbestosis, interstitial pulmonary edema (congestive heart failure), pulmonary areas with poor ventilation and atelectasis or resolving lobar pneumonia.

Expiratory crackles are uncommon but may occur following early inspiratory crackles in diffuse airflow obstruction. Such crackles are evenly spaced and are confined to early inspiration and to mid or late expiration. They differ from the later inspiratory crackles of diffuse interstitial fibrosis or pulmonary edema because they are low-pitched, scanty, loud and are more widely transmitted, especially through the lower lobes.

4. WHEEZES OR RHONCHI

Wheezes or rhonchi are continuous, musical pulmonary sounds resulting from partial airway obstruction. They have a repetitive pattern which is a distinctive feature. Wheezes, can be low or high pitched and are produced when a certain velocity of airflow passes through the almost closed walls of an airway. The pitch of a wheeze is related to the velocity of airflow, being higher with rapid velocity and lower when ventilation is reduced. In severe airway obstruction there may be no wheezing at all.

Wheezing is more common with expiration than with inspiration although inspiratory wheezing may occur in localized rigid lesions and in asthma, as opposed to chronic bronchitis or emphysema.

5. STRIDOR

Stridor is a loud, predominantly inspiratory monophonic musical sound caused by spasm and/or swelling of the vocal chords or trachea, such as occurs with whooping cough, croup, tracheal stenosis, or tumors. It is generated by the same mechanism as the wheeze: an obstruction to air flow. The wheeze has it origin in the bronchi or bronchioles, whereas stridor has its origin in the larynx or trachea.

6. PLEURAL OR FRICTION RUB

Pleural disease may produce a series of interrupted, nonmusical sounds (crackles) due to the friction caused by fibrin inflammation or tumor involving the pleural surfaces. Pleural or friction rub is usually nonmusical, but can become musical if a large area of the chest wall is set into a resonant oscillation. They are heard during inspiration and expiration and disappear when respiration is held, unlike the pericardial rub which is independent of respiration. Increasing pleural fluid may separate the roughened pleural surface and eliminate the crackling. Pleural clicking or crackling sounds are heard in left pneumothorax. They are synchronous with the heart beat and are best heard at the left sternal border. Mediastinal emphysema (pneumomediastinum) can also cause such clicking or crackling noises.

Bruits Mode of Operation

Bruits are the swishing sounds caused by turbulent blood flow in arteries. This type of cardiovascular diagnosis is helpful in identifying occlusive arterial disease. Blood flow through the arteries is silent in patients free of any arterial disease. The preferred embodiment of the present invention is capable of identifying and quantizing the types and sizes of abnormalities of blood vessels. Operation in this mode is similar to the operation described above in that matrices are constructed and compared using a form of signature analysis to identify and diagnose.

Changing the mode key to bruits mode is accomplished by the user simply pressing the Mode key on the keyboard 110. The software locations 412 and 414 of FIG. 4a identify the particular mode of operation of the present invention and invoke the bruits mode. In this mode of operation, the sternum display or lung display is replaced by a body display which indicates the bruits mode of operation. The display also prompts the physician as to which arterial region to apply the chest piece of the stethoscope.

Vessels do not usually produce noises or bruits under normal conditions. With constriction, however, turbulent blood flowing through a vessel produces an audible sound defined as a bruit, and varies in frequency from 10 to 2000 cps. A bruit usually implies an arterial stenosis at or proximal to the site of auscultation. Very severe obstruction may not produce a bruit since blood flow would be minimal.

Evidence of atherosclerotic arterial disease as manifested by an arterial bruit in one region of the body usually indicate that other regions are diseased as well. A soft early systolic bruit is usually noted with a lumen diameter of reduction of 50 percent. With obstruction increased to 60 percent, the bruit becomes louder, holosystolic and higher pitched. At 70-80 percent diameter reduction, the pressure gradient may remain even during diastole, and the bruit may be heard in both systole and early diastole.

The chestpiece of the instrument is applied to the following areas which overlie specific arteries:

1. Anterior cervical areas overlying internal and external carotid arteries.
2. Supraclavicular areas overlying subclavian arteries.
3. Infraclavicular areas overlying axillary arteries.
4. Epigastrium area overlying celiac artery.
5. Abdominal upper guadrants overlying renal arteries.
6. Lumbar area overlying renal arteries.
7. Inguinal areas overlying common femoral arteries.
8. Femoral triangles overlying superficial femoral arteries.
9. Umbilical area overlying aortoiliac bifurcation.
10. Anteromedial thighs overlying superficial femoral arteries.
11. Popliteal Fossae overlying popliteal arteries.

Auscultation is preceded by observing the location of a marker on the display diagram which illustrates the current arterial region to apply the chestpiece. The Capture button is pushed while the user auscultates each area and after inspection of the LCD display, will push the Enter button before advancing to the next region as specified by the diagram on the display. A determination of whether a bruit exists is performed in each location based on minimal frequency characteristics. At the end of the auscultation sequence all waveform patterns along with their specific locations are used for the software analysis.

It will be readily apparent to those skilled in the art that many modifications to the preferred embodiment of the present invention are possible without deviating from the scope and spirit of the present invention. Special conditions employed for the implementation of the preferred embodiment are not intended to be limiting and are easily adaptable to alternate implementations. For example, the control structure of the present invention is generally implemented using microprocessor-based architectures and LSI logic functions. It will be readily understood by those skilled in the art upon reading and understanding this specification and drawings that the control structure of the present invention may be implemented in a wide variety of different ways, including the use of external computer control, ROM microcode control, PLA or PAL logic structures, and other types of hardwired or software controlled state machines. Also, the signature analysis portion of the present invention may be performed in the analog or digital domains.

Although the digital data representing the attributes and characteristics of the body sounds is arranged in the form of a matrix for purposes of comparison, those skilled in the art will recognize that other techniques for comparison and other arrangements for data could be used. For example, instead of using matrices, each characteristic could be serially compared to stored characteristics in the form of a flow diagram. Hence, those skilled in the art will recognize that a matrix is not the only data arrangement for the present invention.

Although specific software configurations and flow diagrams have been illustrated and described for the preferred embodiment of the present invention set forth herein, it will be appreciated by those of ordinary skill in the art that a wide variety of software implementations calculated to achieve the same purpose may be substituted for the specific software descriptions shown. Thus, although conventional subroutines, decisions and control flow have been described, those skilled in the art will readily recognize the substitution of a wide variety of alternate control flows, interrupt-driven routines, external control mechanisms, and the use of hardware control as opposed to software control without deviating from the spirit and scope of the present invention. Those experienced in the electrical and computer arts will readily recognize that the present invention may be implemented in a very wide variety of embodiments.

Those skilled in the art will also recognize the wide variety of diagnostic abilities of the present invention. The techniques described herein are applicable to automatic diagnosis through the use of matrix comparison similar to signature analysis. Those skilled in the medical arts will readily recognize that diagnostic matrices capable of being stored and compared using the present invention can be constructed for any ailment that could be diagnosed through auscultation. The present invention is not limited to auscultation techniques applied only to heart, lung and cardiovascular, but also to gastrointestinal and other body sounds.

While the present invention has been described in connection with a preferred embodiment thereof, it will be understood that many modifications will be readily apparent to those of ordinary skill in the art, and this application is intended to cover any adaptations or variations thereof. Therefore, it is manifestly intended that this invention be limited only by the claims and the equivalents thereof.

What is claimed is:

1. A stethoscope adapted to receive and display body sounds from a plurality of body locations, comprising:
    a microphone adapted to receive said body sounds from said plurality of body locations, said microphone converting each of said body sounds into an electrical signal;
    a memory operatively coupled to said microphone, said memory adapted to store at least one said electrical signal for each of said plurality of body locations;
    location means operatively coupled to said memory for associating each said electrical signal with a corresponding one of said plurality of body locations;
    a display operatively coupled to said memory and to said location means, said display receiving at least one said electrical signal for a selected one of said plurality of body locations and displaying a diagram representative of said selected one of said body locations and a visual representation of said body sounds for said selected one of said body locations; and
    wherein said location means further includes a cursor on said diagram associating at least one said electrical signal with said selected one of said body locations on said diagram.

2. The stethoscope according to claim 1 wherein said diagram indicates a sternum and a plurality of increment positions near the sternum associated with each of said body locations and from which said selected one of said plurality of body locations can be identified.

3. A stethoscope adapted to receive and display body sounds from a plurality of body locations, comprising:
    a microphone adapted to receive said body sounds from said plurality of body locations, said microphone converting each of said body sounds into an analog electrical signal;
    an analog-to-digital convertor operatively coupled to said microphone, said analog-to-digital converter converting said analog electrical signal into a digital electrical signal;
    a memory operatively coupled to said converter, said memory adapted to capture a time interval of said digital electrical signal and adapted to store at least one said digital electrical signal corresponding to said time interval representative of said body sounds for each of said plurality of body locations;
    location means operatively coupled to said memory for associating each said digital electrical signal with a corresponding one of said plurality of body locations;
    a display operatively coupled to said memory and to said location means, said display receiving said digital electrical signal for a selected one of said plurality of body locations and displaying a diagram representative of said selected one of said body locations and a visual representation of said digital electrical signal for said selected one of said body locations;
    display control means connected to said memory and to said display for controlling and manipulating said visual representation of at least one said digital electrical signal on said display; and
    wherein said location means further includes a cursor on said diagram associating at least one said digital electrical signal with said selected one of said body locations on said diagram.

4. The stethoscope according to claim 3 wherein said diagram indicates a sternum and a plurality of increment positions near the sternum associated with each of said body locations and from which said selected one of said plurality of body locations can be identified.

5. A stethoscope adapted to receive, store and display a body sound from each of a plurality of body locations, comprising:
   a microphone;
   input means attached to said microphone for receiving the body sound from each of the plurality of body locations and for converting each of the body sounds into an electrical signal;
   memory means, operatively coupled to said input means, for storing said electrical signal for each of said plurality of body locations;
   control means, operatively coupled to said memory means and to said input means, for associating each said electrical signal with a corresponding one of said plurality of body locations;
   display means, operatively coupled to said memory means an d said control means, for displaying a visual representation of a selected one of said body sounds, and further including indicator means for indicating from which of said plurality of body locations said selected one of said body sounds was received.

6. The stethoscope according to claim 5 wherein said indicator means further includes:
   a diagram means for displaying a graphical representation of at least a portion of a human body;
   cursor means for indicating on said diagram means for which of said plurality of body locations said selected one of said body sounds was received.

7. The stethoscope according to claim 6 wherein said body sounds are heart sounds and said graphical representation of at least a portion of a human body is a sternum diagram.

8. The stethoscope according to claim 6 wherein said body sounds are lung sounds and said graphical representation of at least a portion of a human body is a lung diagram.

9. The stethoscope according to claim 5 further including display control means, operatively connected to said memory means and said display means, for controlling and manipulating said visual representation of said selected one of said body sounds being displayed on said display means.

10. The stethoscope according to claim 5 wherein a specific order of ausculation is followed, and wherein said indicator means is further for prompting a user from which of said plurality of body locations a next body sound in said specific order of ausculation should be received.

11. The stethoscope according to claim 6 wherein a specific order of ausculation is followed, and wherein said cursor means is further for pointing to one of said plurality of body locations on said diagram means, from which location a next body sound in said specific order of auscultation should be received.

12. The stethoscope according to claim 5 wherein said indicator means is further for being manipulated by a user to indicate from which of said plurality of body locations the user intends to next receive a body sound.

13. The stethoscope according to claim 6 wherein said cursor means is further for being manipulated by a user to point to one of said plurality of body locations on said diagram means to indicate from which of said plurality of body locations the user intends to next receive a body sound.

14. A stethoscope adapted to receive and display body sounds from a body locations, comprising:
   a microphone adapted to receive said body sounds from said body location, said microphone converting each of said body sounds into an electrical signal;
   a memory operatively coupled to said microphone, said memory adapted to store at least one said electrical signal for said body location; and
   a display operatively coupled to said memory, said display receiving at least one said electrical signal for said body location and displaying a diagram representative of said body location and a visual representation of said body sounds for said body location; and
   wherein said diagram further includes a cursor associating at least one said electrical signal with said body location on said diagram.

* * * * *

UNITED STATES PATENT AND TRADEMARK OFFICE
CERTIFICATE OF CORRECTION

PATENT NO. : 5,218,969

DATED : June 15, 1993

INVENTOR(S) : Mark S. Bredesen et al

It is certified that error appears in the above-indentified patent and that said Letters Patent is hereby corrected as shown below:

On title page, item [75] "Elliot" should read --Elliott--

In column 5, line 64, insert --*Diagnose-- before the work "Diagnose" therefore.

In column 6, line 39, "hz" should be --Hz-- therefore.

In column 6, line 42, "Khz" should be --KHz-- therefore.

In column 7, line 24, "generate" should read --generates-- therefore.

In column 8, line 53, insert --may be helpful for a full understanding of the present-- after the word "3e" therefore.

In column 12, line 68, "determine" should read --determines-- therefore.

In column 20, line 64, "is" should read --are-- therefore.

UNITED STATES PATENT AND TRADEMARK OFFICE
CERTIFICATE OF CORRECTION

PATENT NO. : 5,218,969

DATED : June 15, 1993

INVENTOR(S) : Mark S. Bredesen et al.

It is certified that error appears in the above-identified patent and that said Letters Patent is hereby corrected as shown below:

In column 23, line 27, "is" should read --in-- therefore.

In column 25, line 55, "Third" shouldn't start a new paragraph, should continue on line 54.

In column 26, line 45, "heart" should read --heard-- therefore.

In column 31, line 59, "restrition" should read --restriction-- therefore.

In column 33, line 39, "unsubsided" should read --subsided-- therefore.

In column 33, line 49, "infraction" should read --infarction-- therefore.

In column 34, line 12 "middiastolic" should read --mid-diastolic-- therefore.

In column 34, line 27, "auscoltatory" should read --auscultatory-- therefore.

In column 34, line 33, insert --be-- after the word "can" therefore.

In column 34, line 65, "way forms" should read --wave forms-- therefore.

In column 41, line 18 (claim 5), "an d" should read --and-- therefore.

UNITED STATES PATENT AND TRADEMARK OFFICE
CERTIFICATE OF CORRECTION

PATENT NO. : 5,218,969

DATED : June 15, 1993

INVENTOR(S) : Mark S. Bredesen et al.

It is certified that error appears in the above-identified patent and that said Letters Patent is hereby corrected as shown below:

In column 41, line 26 (claim 6), delete "a" after the word "includes:" therefore.

In column 41, line 29 (claim 6), "for" should read --from-- therefore.

In column 42, lines 4 and 7 (claim 10), "ausculation" should read --auscultation-- therefore.

In column 42, line 10 (claim 11), "ausculation" should read --auscultation-- therefore.

In column 42, line 26 (claim 14), "locations" should read --location-- therefore.

Signed and Sealed this

Twenty-ninth Day of November, 1994

Attest:

BRUCE LEHMAN

*Attesting Officer*  *Commissioner of Patents and Trademarks*